US008532778B2

(12) United States Patent  
Lin

(10) Patent No.: US 8,532,778 B2  
(45) Date of Patent: Sep. 10, 2013

(54) RESTORING COUGH USING MICROSTIMULATORS

(75) Inventor: Vernon Lin, Cerritos, CA (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 1779 days.

(21) Appl. No.: 11/845,713

(22) Filed: Aug. 27, 2007

(65) Prior Publication Data

US 2008/0051851 A1 Feb. 28, 2008

Related U.S. Application Data

(60) Provisional application No. 60/840,742, filed on Aug. 28, 2006.

(51) Int. Cl.  
*A61N 1/02* (2006.01)

(52) U.S. Cl.  
USPC ............................................. 607/42; 607/117

(58) Field of Classification Search  
USPC ................................................... 607/42, 117  
See application file for complete search history.

(56) References Cited

U.S. PATENT DOCUMENTS

| 5,143,067 | A | 9/1992 | Rise et al. |
| 5,193,539 | A | 3/1993 | Schulman et al. |
| 5,193,540 | A | 3/1993 | Schulman et al. |
| 5,312,439 | A | 5/1994 | Loeb et al. |
| 5,324,316 | A | 6/1994 | Schulman et al. |
| 5,405,367 | A | 4/1995 | Schulman et al. |
| 5,591,216 | A | 1/1997 | Testerman et al. |
| 6,051,017 | A | 4/2000 | Loeb et al. |
| 6,175,764 | B1 | 1/2001 | Loeb et al. |
| 6,214,032 | B1 | 4/2001 | Loeb et al. |
| 6,345,202 | B2 | 2/2002 | Richmond et al. |
| 6,795,737 | B2 | 9/2004 | Gielen et al. |
| 6,836,685 | B1 | 12/2004 | Fitz |
| 6,871,099 | B1 | 3/2005 | Whitehurst et al. |
| 6,941,171 | B2 * | 9/2005 | Mann et al. ..................... 607/39 |
| 2004/0015205 | A1 | 1/2004 | Whitehurst et al. |

OTHER PUBLICATIONS

Burridge et al., "A preliminary clinical study using RF BION® microstimulators to facilitate upper limb function in hemiplegia" *Adv. Clin. Neuro. Rehab.*, 4(2): 27-28-1471, 2004.

DiMarco et al., "Electrical activation of the expiratory muscles to restore cough," *Am. J. Respir. Crit. Care Med.*, 151(5):1466-1471, 1995.

DiMarco et al., "Pattern of expiratory muscle activation during lower thoracic spinal cord stimulation," *J. Appl. Physiol.*, 86(6):1881-1889, 1999.

(Continued)

*Primary Examiner* — Christopher D Koharski  
*Assistant Examiner* — Jeremiah Kimball  
(74) *Attorney, Agent, or Firm* — Klarquist Sparkman, LLP

(57) ABSTRACT

A method of inducing forced expiration in a subject is disclosed. The method can include percutaneously placing an injectable microstimulator adjacent at least one thoracic spinal nerve that innervates an intercostal muscle. For example, the microstimulator is placed within 8 cm externally of a neuroforamen through which the spinal nerve emerges from a thoracic vertebra. The method can also entail applying a stimulating electrical current from the microstimulator to the thoracic spinal nerve at a sufficient intensity and duration to induce a forced contraction of the intercostal muscle innervated by that spinal nerve.

24 Claims, 13 Drawing Sheets

(56) References Cited

OTHER PUBLICATIONS

DiMarco et al., "Mechanism of expiratory muscle activation during lower thoracic spinal cord stimulation," *J. Appl. Physiol.*, 92(6):2341-2346, 2002.

DiMarco, AF., "Restoration of respiratory muscle function following spinal cord injury. Review of electrical and magnetic stimulation techniques," *Respir. Physiol. Neurobiol.*, 147(2-3):273-287, 2005.

DiMarco et al., "Spinal cord stimulation: a new method to produce an effective cough in patients with spinal cord injury," *Am. J. Respir. Crit. Care Med.*, 173(12):1386-1389, 2006.

Lin et al., "Functional magnetic stimulation of expiratory muscles: a noninvasive and new method for restoring cough," *J. Appl. Physiol.*, 84:1144-1150, 1998.

Lin et al., "Functional magnetic stimulation for restoring cough in patients with tetraplegia," *Arch. Physic. Med. Rehabil.*, 79(5):517-522, 1998.

Loeb et al., "The BION devices: injectable interfaces with peripheral nerves and muscles," *Neurosurg. Focus*, 20(5):E2, 9 pages, 2006.

* cited by examiner

RESTORING COUGH USING MICROSTIMULATORS

CROSS-REFERENCE TO RELATED APPLICATION

This application claims the benefit of priority under 35 U.S.C. §119 to U.S. Provisional Application No. 60/840,742 filed on Aug. 28, 2006, which is incorporated herein by reference in its entirety

STATEMENT OF GOVERNMENT SUPPORT

This invention was funded by a United States Veterans Affairs Rehabilitation Research and Development Merit Review Grant. Accordingly, the government has certain rights in this invention.

FIELD

The present disclosure relates to the field of magnetic stimulation, and in particular to methods utilizing magnetic stimulation to generate an effective expiratory function such as a cough.

BACKGROUND

Respiratory complications are the most common cause of morbidity and mortality following spinal cord injury (SCI). These complications arise partly due to the loss of supraspinal control over the expiratory muscles, such as abdominal and lower intercostal muscles. Disrupted neuromuscular central nervous system control of the expiratory muscles interferes with producing an effective cough to clear airway secretions, resulting in respiratory tract infections.

Current management of expiratory dysfunction in subjects with SCI includes passive postural drainage, tracheal suctioning, and assisted or "quad" cough. Each method has a varying degree of effectiveness and all require active assistance. Further, functional electrical stimulation (FES) has also been utilized to produce an expiratory function by direct stimulation of the spinal cord. FES is a technique that uses electrical currents to activate nerves innervating extremities affected by paralysis resulting from spinal cord injury (SCI), head injury, stroke or other neurological disorders. For example, FES was shown to produce high positive airway pressures ($P_{aw}$) in animal studies when a plate electrode was applied to the epidural surface of the lower thoracic spinal cord in the animal (DiMarco et al., Am. J. Respir. Crit. Care Med. 151: 1466-1471, 1995). Maximal expiratory pressure generation occurred when stimulation was applied in the area of T9-T10 thoracic vertebrae of the animal. In a similar human study, simultaneous stimulation at the T9 and L1 levels of a tetraplegic subject produced a maximal $P_{aw}$ of 132$H_2O$ and peak expiratory flow of 7.4 L/s (DiMarco et al., Am. J. Respir. Crit. Care Med. 173(12): 1386-1389, 2006).

Functional magnetic stimulation (FMS) has also been demonstrated to produce an expiratory function by stimulating the lower thoracic spinal nerve root in a human subject (Lin et al., J. Appl. Physiol. 84: 1144-1150, 1998; Lin et al., Arch. Physic. Med. Rehabil. 79: 517-22, 1998). FMS is achieved by an external application of electromagnetic energy to the spinal cord. For example, maximal expiratory pressure generated by FMS was 83.6±16.4 cm $H_2O$ when a magnetic coil was placed at T9 spinous process in able-bodied subjects (Lin et al., J. Appl. Physiol. 84: 1144-1150, 1998). Further, when a similar stimulation protocol was applied to subjects with SCI, FMS of the expiratory muscles also produced a substantial expiratory pressure of 68.2±24.1 cm $H_2O$ in which placement of the magnetic coil at the T10-T11 spinous process produced the highest expiratory pressure and flow (Id.).

It would be advantageous to provide improved methods of minimally-invasive neuromuscular stimulation to produce expiratory function without requiring major surgery in order to minimize infection and facilitate maintenance of the stimulation device. The prior direct implantation of epidural FES electrodes require surgical exposure of the central nervous system, with attendant risks of infection and additional trauma. Although FMS avoids those drawbacks, it requires the use of inconvenient external magnets and associated equipment.

SUMMARY

An improved method of inducing forced expiration in a subject is disclosed. In one embodiment, an injectable microstimulator is placed adjacent at least one thoracic spinal nerve that innervates an intercostal muscle. For example, the microstimulator can be placed within 8 cm externally of a neuroforamen through which the spinal nerve emerges from a thoracic vertebra. The method can also entail applying a stimulating electrical current from the microstimulator to the thoracic spinal nerve at a sufficient intensity and duration to induce a forced contraction of the intercostal muscle innervated by that spinal nerve. In particularly effective examples, the first and second microstimulators are placed adjacent first and second contralateral nerves for at least three levels from T8 through L1, for example three or more of any combination of T9, T10, T11, T12 and L1. The microstimulators can also be remotely activated to apply the current, without the use of lead lines into the body.

The foregoing and other features and advantages will become more apparent from the following detailed description of several embodiments, which proceeds with reference to the accompanying figures.

DETAILED DESCRIPTION OF SEVERAL EMBODIMENTS

There are more than two hundred thousand individuals with SCI living in the United States alone. About half of these subjects are not able to produce an effective cough to clear airway secretions because the SCI disrupts the neuromuscular control of the expiratory muscles. In the absence of effective airway maintenance, respiratory tract infections often develop. These infections can develop into debilitating and life threatening pneumonias. Respiratory tract infections have become an increasingly severe medical problem in an era of antibiotic resistant pathogens that are less easily treated with antimicrobial medications. In addition, chronic antimicrobial prophylaxis is one factor that leads to the development of drug resistant bacteria.

Figure 1A:
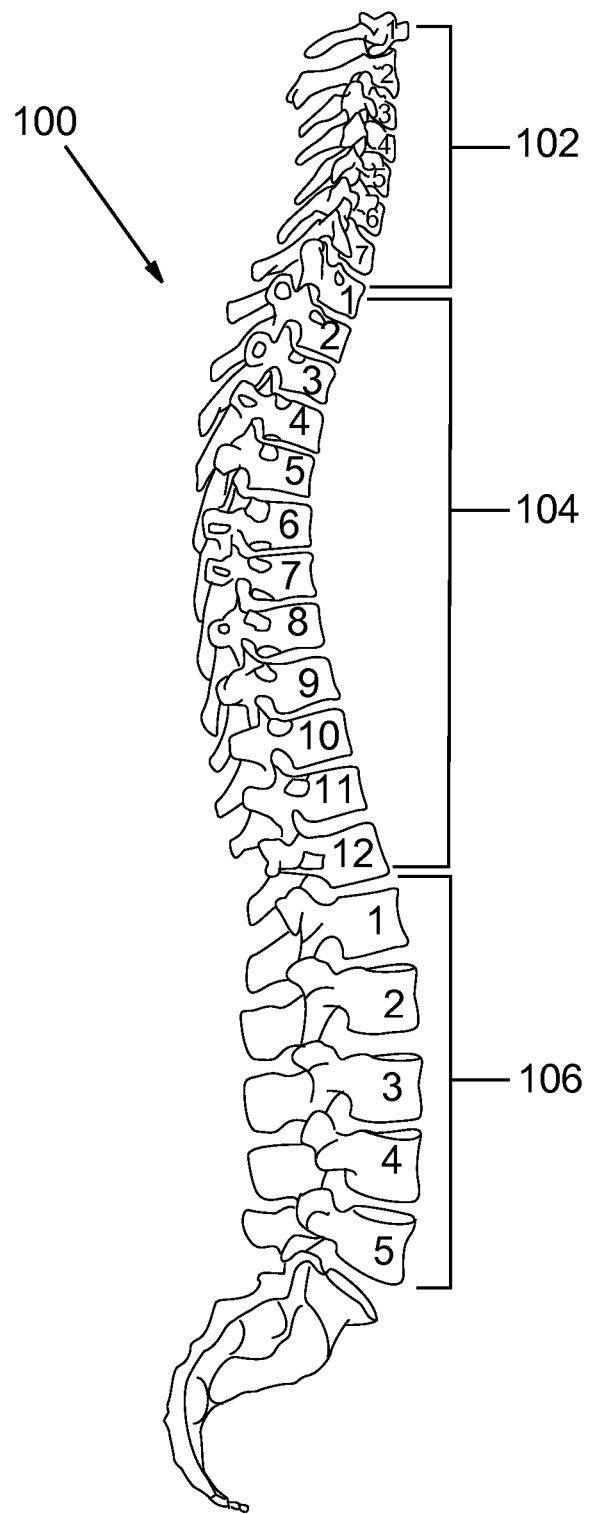
FIG. 1A is a side view of a human vertebral column illustrating the position of cervical vertebrae 1-7, thoracic vertebrae 1-12 and lumbar vertebrae 1-5.

When the spinal cord is damaged, the respiratory muscles below the level of injury become paralyzed and are devoid of supraspinal control. FIG. 1A illustrates a human vertebral column 100. As demonstrated in FIG. 1A, the human vertebral column includes seven cervical vertebra denoted collectively as 102, twelve thoracic vertebrae denoted collectively as 104 and five lumbar vertebrae denoted collectively as 106. Subjects with paraplegia at level T12 and below have essentially no respiratory dysfunction. With levels of injury ascending from T12 through T5, there is a progressive loss of forceful expiration and cough, while with levels of injury ascending from T5 through T1 the volitional function of intercostal muscles is lost. Subjects with levels of tetraplegia from C8 through C4 have no intercostal or abdominal muscle activity, their inspiratory effort depends upon diaphragmatic contractions.

Figure 1B:
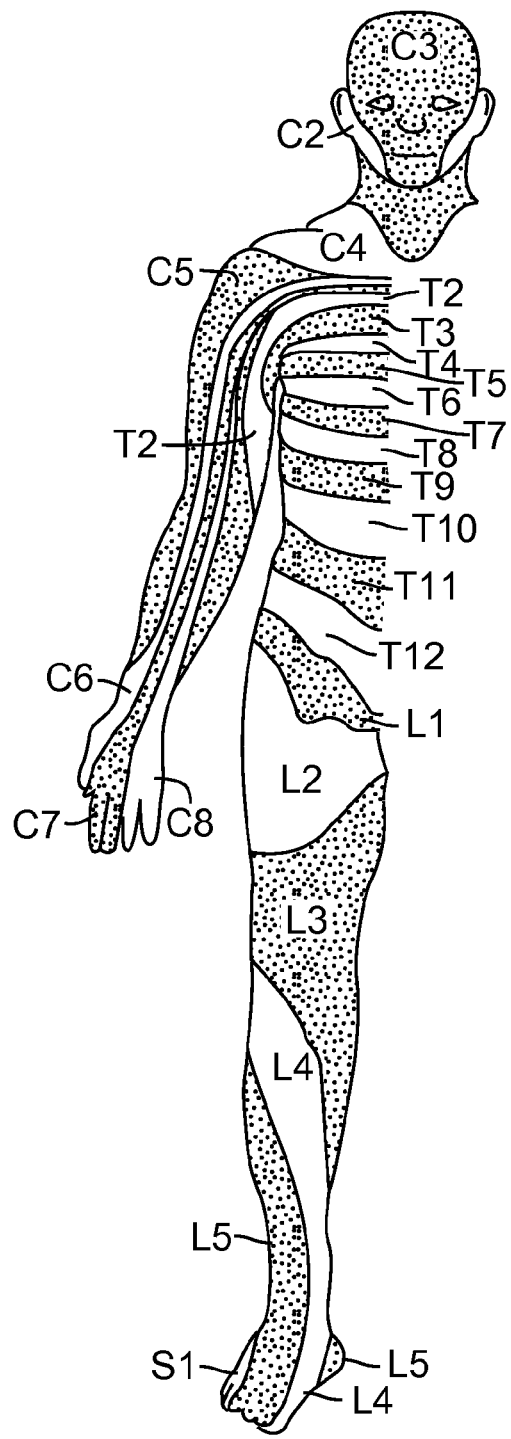
FIG. 1B is a dermatome map of a human subject providing a front view of the different areas of the body innervated by corresponding spinal nerves.
Figure 1C:
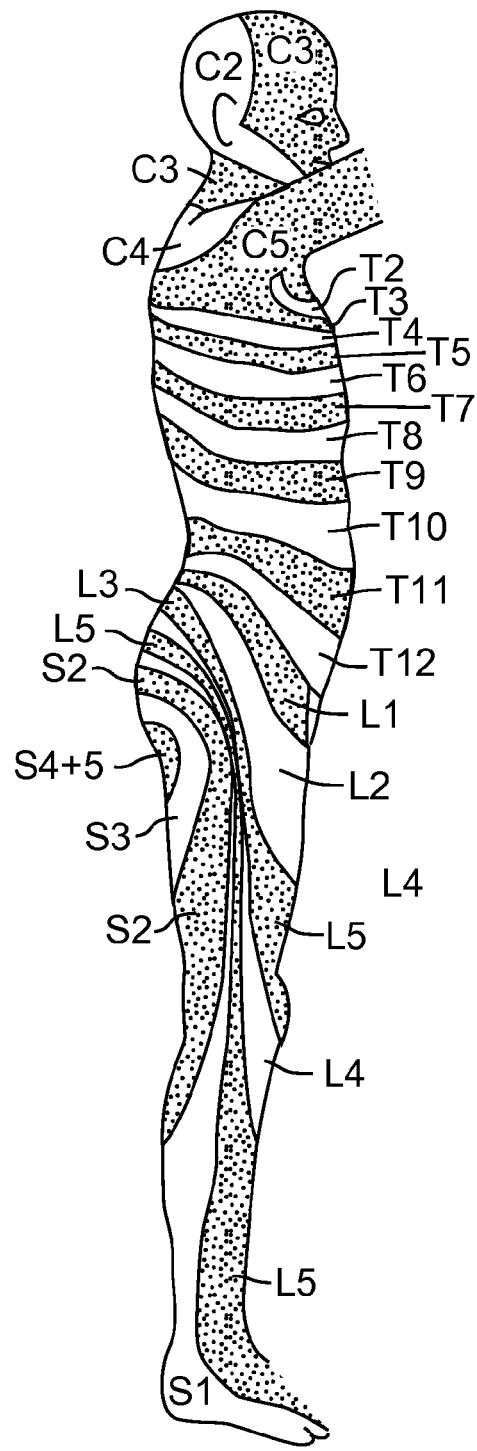
FIG. 1C is a side view of the different dermatome fields of FIG. 1B.

The dermatome map as illustrated in FIGS. 1B and 1C is clinically useful in determining the level of spinal cord injury. Lesions of one or more spinal nerves are associated with corresponding patterns of neurological defects such as muscle weakness or loss of sensation to the skin innervated by those nerves. Thus, identification of the particular region in which sensation is lost allows one to localize the spinal cord lesion. FIGS. 1B and 1C illustrate the different dermatomes which each spinal nerve innervates. For example, a loss of sensation in a subject's second and third fingers is indicative of a C7 spinal cord injury. Although the dermatomes are shown as if there were distinct borders between the adjacent dermatomes, substantial overlap exists from segment to segment. This overlap limits the usage of dermatome maps because the posterior roots of an entire segment of the spinal cord can be destroyed without causing significant loss of sensation to the skin.

Pulmonary function tests in subjects with cervical cord injury often reveal marked impairment. Paralysis of both inspiratory and expiratory muscles produce a reduced vital capacity (VC), little or no expiratory reserve volume, and the VC is equal to the inspiratory capacity (Hemingway et al., *J. Clin. Invest.* 37: 773-782, 1985; James et al., *Chest* 71: 59-64, 1977; McMichan et al., *JAMA* 243: 528-31, 1980). Decreased pulmonary function is associated with a predisposition to respiratory complications, such as bronchitis, pneumonia, and colonization with drug resistant organisms such as a methicillin resistant staphylococcus (MRSA).

The present disclosure provides important methods for minimally-invasive neuromuscular stimulation to produce an expiratory function such as a cough. The currently disclosed methods utilize microstimulators of a size and a shape that allow the microstimulators to be implanted directly at the stimulation site by a minimally-invasive procedure, such as percutaneous introduction, for example through an instrument such as a needle or trocar. Thus, the disclosed methods allow microstimulators to be efficiently implanted, minimizing risks of infection, hemorrhage, or device failure while reducing the time required to recover from the implantation procedure. In disclosed embodiments, the microstimulators are capable of being remotely activated without lead lines connected to a power source. Such minimally-invasive microstimulators utilized in the present methods minimize the threat of infection, skin breakdown or tissue damage associated with the use of electrodes and long electrical leads that must be placed in multiple surgical sites in subjects who have circulatory or neurological problems. In addition, implantation of the microstimulators can be performed in an outpatient procedure, and faster recovery from the procedure permits use of the stimulators more quickly. The convenience and minimally-invasive features of the presently disclosed methods provide important advantages for the use of functional and therapeutic magnetic stimulation to generate an effective expiratory function such as a cough.

Furthermore, use of the microstimulators was found to be as effective at generating an expiratory function as more invasive technologies, such as FES of the ventral root. Therefore, the instant methods may replace many of the currently employed devices that require active assistance or FES by providing a more physiologically compatible, minimally-invasive method of restoring cough function and removing airway secretions in SCI subjects. Subjects with expiratory muscle impairments due to other pathologies (such as degenerative neuromuscular disorders) may also benefit from the disclosed methods of stimulatory expiratory function.

I. ABBREVIATIONS cm: centimeters
EMG: electromyogram
$f_c$: centroid frequency
Hz: hertz
IM intramuscular injection
mA: milliamps
mHz: megahertz
$P_{aw}$: positive airway pressure
SCI: spinal cord injury
V: volts
VC: vital capacity

II. TERMS

Unless otherwise explained, all technical and scientific terms used herein have the same meaning as commonly understood by one of ordinary skill in the art to which the disclosed subject matter belongs. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Although methods and materials similar or equivalent to those described herein can be used in the practice or testing of the present disclosure, suitable methods and materials are described below. It is further to be understood that any quantitative values are approximate whether the word "about" or "approximately" or the like are stated or not. In addition, the materials, methods, and examples described herein are illustrative only and not intended to be limiting.

In order to facilitate review of the various embodiments of this disclosure, the following explanations of specific terms are provided:

Contralateral nerves: Nerves that originate or innervate muscles on opposite sides of the spinal cord.

Dermatome field: A segmental field of the skin innervated by a spinal nerve.

Inducing forced expiration: Expiration caused by an artificial method such as a stimulating device which results in the contraction of the intercostal or abdominal muscles to generate forced expiration such as a cough. For example, a microstimulator induces forced expiration by stimulating a thoracic spinal nerve at a sufficient intensity and duration to induce a forced contraction of the intercostal muscle innervated by that spinal nerve to produce a cough.

Intercostal muscles: The intercostal muscles are found between the ribs and include two kinds of intercostal muscles, the internal intercostal muscles and the external intercostal muscles. The thoracic cavity can be enlarged (and air inspired) by raising the rib cage with the external intercostal muscles. The internal intercostal muscles are situated deep to (inside) the external intercostal muscles, and contraction of the internal intercostals pulls the ribs together to increase intrathoracic pressure and force air out of the lungs.

Intercostal nerves: The thoracic spinal nerves T3 through T12 that innervate the corresponding intercostal muscles.

Microstimulator: A stimulator which is of a size and a shape suitable for percutaneous implantation through the lumen of a trocar-based insertion device or laparoscopic instrument. For example, the microstimulator is approximately 2 mm to 3 mm in diameter and approximately 16 mm in length to allow for percutaneous insertion with an insertion device including a 12-gauge trocar needle. A microstimulator is of a size that permits placement in or near the target structures to be stimulated. For example, the microstimulator is of a size that allows the microstimulator to be placed within 8 cm externally of a neuroforamen through which the spinal nerve emerges from a thoracic vertebra. In an example, the microstimulator is powered by inductive coupling of energy from an externally generated magnetic field. In an additional example, the microstimulator is capable of being programmed. For instance, the microstimulator is capable of receiving and transmitting data by modulated radio-frequency telemetry.

Minimally-invasive procedure: A procedure that requires a generally small incision at the surface tissue of a subject. In an example, a minimally-invasive incision is 1 to 1.5 cm in size. In a further example, a minimally-invasive only requires needle-puncture of the skin to perform the procedure. Such a minimally-invasive procedure is referred to herein as a "percutaneous" procedure.

Neuroforamen: The neuroforamen are passageways that are naturally formed on either side (left, right) between an upper and lower vertebra. In between each upper and lower vertebra is an intervertebral disk. The size of the neuroforamen is determined by the height of the intervertebral disk that separates the two vertebrae.

Percutaenous: A medical procedure in which access to inner organs or other tissue is done via a needle-puncture of the skin, rather than by a surgical incision in which inner organs or tissue is exposed.

Spinal nerve: A spinal nerve generally refers to the mixed spinal nerve, which is formed from the dorsal and ventral roots that come out of the spinal cord. The spinal nerve is the portion that passes out of the vertebrae through the neuroforamen. For example, thoracic spinal nerves T3 through T12 innervate T3 through T12 intercostal muscles.

III. DESCRIPTION OF SEVERAL EMBODIMENTS

Methods of Inducing Forced Expiration. Methods of inducing an expiratory function in a subject are disclosed, for example, by inducing a cough in a subject with a spinal cord injury. In one embodiment, forced expiration is achieved by percutaneously placing an injectable microstimulator adjacent at least one thoracic spinal nerve that innervates an intercostal muscle.

Figure 2:
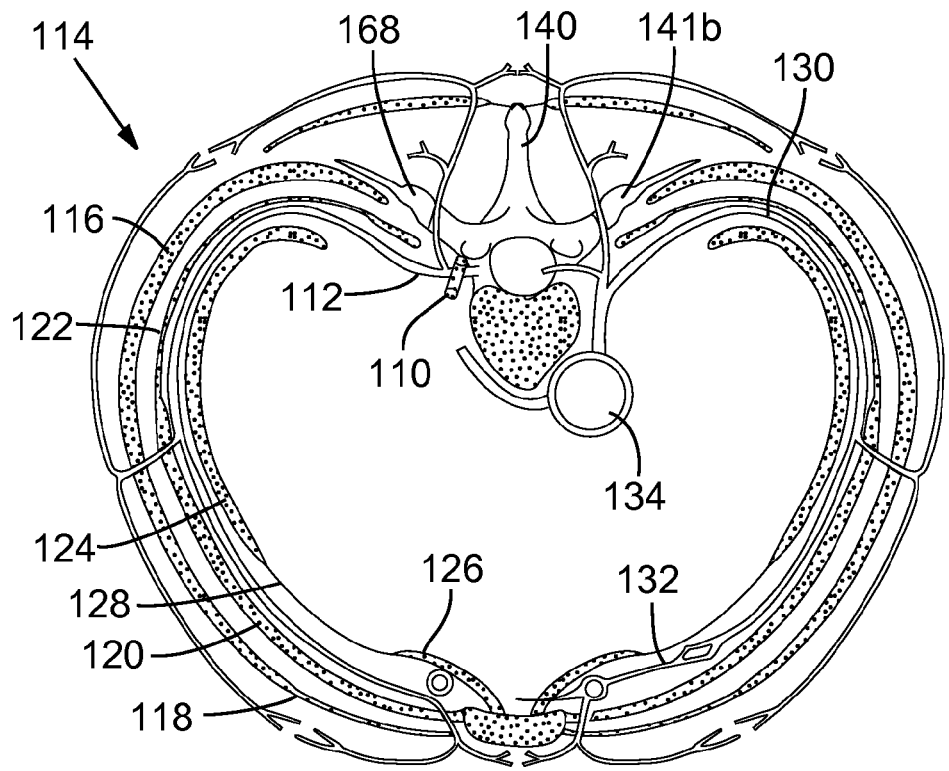
FIG. 2 is a cross-sectional schematic view of a human intercostal space illustrating the position of a microstimulator relative to an intercostal nerve.
Figure 3:
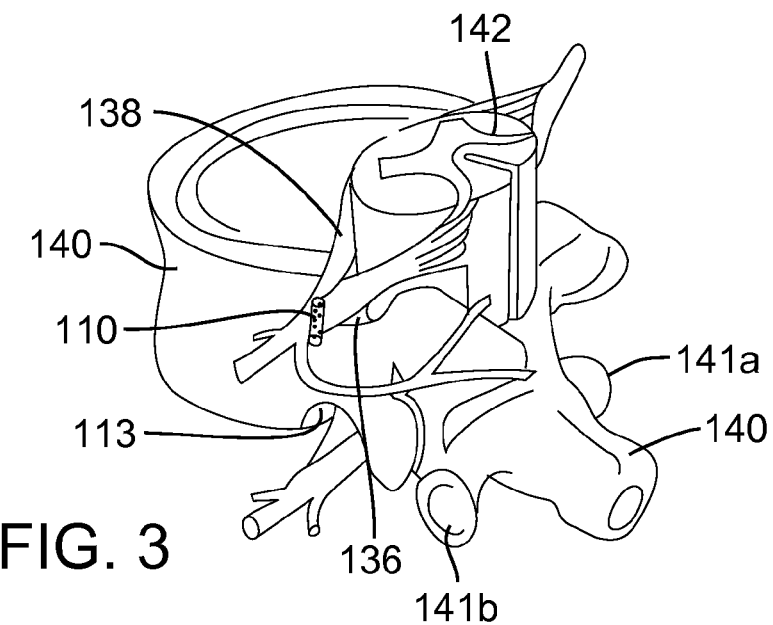
FIG. 3 is a perspective schematic view of a single spinal segment illustrating the position of a microstimulator in relation to a neuroforamen and a spinal nerve.

FIGS. 2 and 3 provide examples of the position of an implanted microstimulator 110 in relation to a spine, which includes a spinous process 140 and transverse processes 141a, 141b. As illustrated in FIG. 2, the intercostal space 114 includes the following muscular layers and membranes: an external intercostal muscle 116 and membrane 118; an internal intercostal muscle 120 and membrane 122; and an innermost intercostal 124 and transversus thoracis 126 muscles and a membrane 128 connecting the two. The intercostal vessels such as the posterior intercostal artery 130 and the anterior intercostal artery 132 travel in the plane between the internal intercostal muscle 120 and innermost layers of muscle such as the innermost intercostal 124 and transversus thoracis 126 muscles. The posterior intercostal artery 130 is a branch of the aorta 134 whereas the anterior intercostal artery 132 is a branch of the internal thoracic artery.

FIG. 2 illustrates placement of microstimulator 110 at the bifurcation of intercostal nerve 112 soon after the nerve emerges from the neuroforamen 113, but before it splits into its ventral and posterior branches. The ventral branch is also known as the intercostal nerve, and is the target of the electrical stimulation with the microstimulator. However, the microstimulator can be placed either proximate or distal to the bifurcation to stimulate contraction or the external intercostal muscles and produce forced expiration (a cough).

In an example, the implantation site for the microstimulator is located by an insertion tool that includes a percutaneous stimulation probe used to identify the locations along the intercostal nerves. An optimal implantation site for a microstimulator is located by percutaneously inserting the stimulating probe 168 at a certain depth and distance lateral to the spinous process 140 and systematically stimulating spinal nerves such as spinal nerves between T6 and L1 vertebra with current pulses. Once the desired position is reached, the stimulation probe is removed and a microstimulator is inserted through the lumen of the insertion tool to the position identified by the stimulating probe. The microstimulator position can be slightly adjusted after insertion with the insertion tool.

In an example, the microstimulator is inserted into a human subject from a surface location about 2-8 cm (for example 2-7 cm) lateral to the spinous process toward the inferior vertebral notch, with the goal of implanting the microelectrode on the vertebral or intercostal nerve about 1-8 cm (for example less then 8 cm, or within 2-7 cm) lateral to the neuroforamen through which the spinal nerve emerges from the spine. These distances can vary, depending on the anatomy of the subject in whom they are implanted, or the species of the subject. In a dog, for example, the microstimulator is preferably introduced about 2-7 cm lateral to the spinous process, with the goal of implanting it about 1-3 cm distal to the neuroforamen, for example about 1.5 cm distal to the neuroforamen. In an additional example, the microstimulator is positioned from a surface position up to 8 cm lateral to the spinous process 140. The microelectrodes can be percutaneously introduced along a path similar to the pathway of a spinal injection needle to perform a nerve injection. The introducer is, for example, inserted between the lateral processes 141a, 141b toward the inferior vertebral notch 113 that defines the neuroforamen. The introducer can also be directed toward the inferior border of the nerve along which the intercostal nerve is generally found. Test stimulation current can be used and repeated until the optimal implantation site is located. Optimal placement is reached by comparing expiratory pressures generated by placing the microstimulator in different locations.

Figure 6:
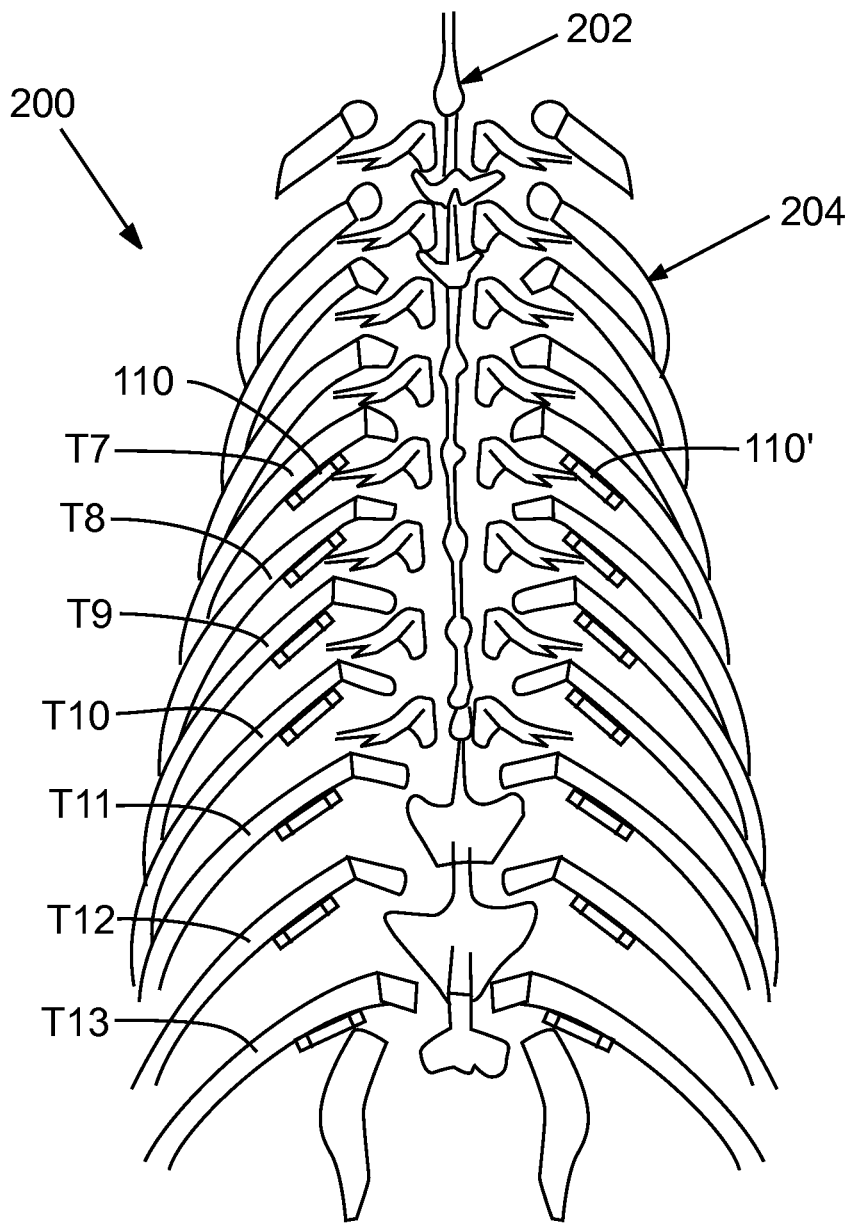
FIG. 6 is a schematic view of a canine vertebral column and rib cage with microstimulators bilaterally positioned at the T7-L1 vertebrae levels.
Figure 7:
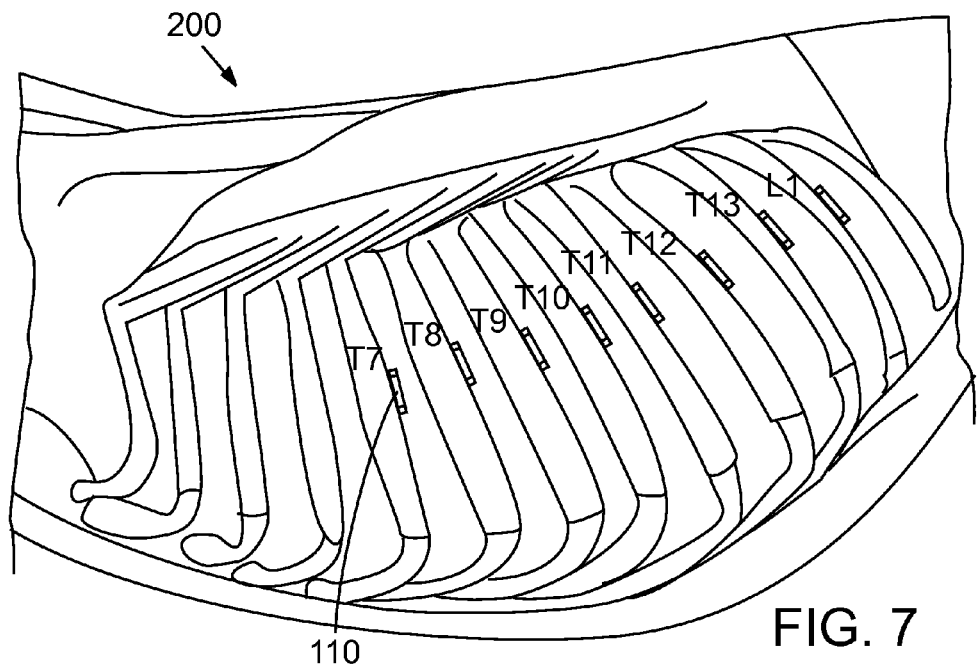
FIG. 7 is a side view of the canine rib cage of FIG. 6 illustrating the position of eight microstimulators along the mid-axillary line.

In an additional example, a first microstimulator 110 and a second microstimulator 110' are percutaneously inserted adjacent a first and a second contralateral thoracic nerves such as intercostal thoracic nerves, including contralateral thoracic nerves at the same level. As illustrated in FIGS. 6 and 7 in a dog, the first and second contralateral thoracic nerves are at the same thoracic level such as thoracic level T8. In another example, the first microstimulator 110 and second microstimulator 110' are placed adjacent first and second contralateral nerves of at least three thoracic levels from T8 through T12 in a species that has intercostal nerves at that level (such as a dog or human). In a further example, the first microstimulator 110 and second microstimulator 110' are placed adjacent first and second contralateral nerves of at least four thoracic levels including thoracic levels T9, T10, T11 and T12. In a still further example, the first microstimulator 110 and second microstimulator 110' are placed against first and second contralateral nerves of at least T8, T9, T10, T11, T12 and L1.

The disclosed methods can also entail applying a stimulating electrical current from the microstimulator to the thoracic spinal nerve at a sufficient intensity and duration to induce a forced contraction of the intercostal muscle innervated by that spinal nerve. In the various embodiments, the stimulating electrical current is applied from the microstimulators to the spinal nerves at a sufficient intensity and duration to induce a forced contraction of the intercostal muscles innervated by those spinal nerves. For example, the stimulating electrical current provides asymmetric biphasic constant-current pulses having a frequency range of approximately 5 to approximately 50 Hz, burst lengths ranging from about a tenth of a second to about ten seconds, stimulation intensity ranging from about 3 to 30 milliamps, and a pulse width of about 200 microseconds. In another example, the stimulation parameters include a frequency of 20 Hz and a stimulation intensity of 8.1 mA to generate an expiratory function that mimics a cough.

The specific stimulation parameters may vary depending upon the needs of the subject. For example, a subject with a T2 level spinal cord injury may require more intense stimulation parameters than a subject with a T10 level spinal cord injury.

Figure 4:
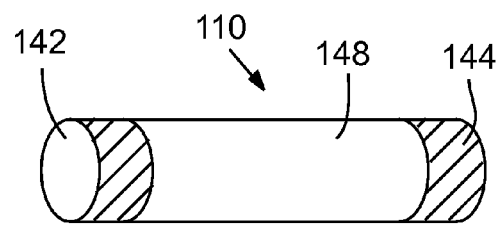
FIG. 4 is a perspective view of a microstimulator for stimulating expiratory function in a subject.

FIG. 4 provides an example of a microstimulator which can be employed to stimulate an expiratory function with the disclosed methods. As illustrated in FIG. 4, the microstimulator 110 is a generally cylindrical device. The microstimulator 110 is of a size and a shape which allows minimally-invasive insertion. For example, the microstimulator is between 2 to 4 mm in diameter and approximately 16 mm in length. The microstimulator 110 includes a first end 142 and a second end 144, and each end of the microstimulator is provided with an electrode (illustrated with cross-hatching in the drawing). In one example, the electrodes include a reference electrode on the first end 142 and an active electrode at the second end 144. This configuration allows electrical signals delivered to nerves to travel away from the stimulation location along the nerve in both directions. The electrodes can be formed of a noble or refractory metal or compound such as platinum, iridium, tantalum, titanium, titanium nitride, niobium, or alloys thereof, to avoid electrolysis, corrosion or other electrochemical reactions that could cause damage to the device or surrounding tissue/nerve. The shape of the microstimulator as well as the number, shape and orientation of the electrodes can vary depending upon the stimulation and therapy desired. For example, additional configurations for the microstimulator include disks, spheres, and helical structures. Possible configurations for the electrodes include rectangular, semi-spherical, arcs, bands/rings, or any other shape that allows the electrodes to be distributed around and/or along the surface of the microstimulator.

Figure 5:
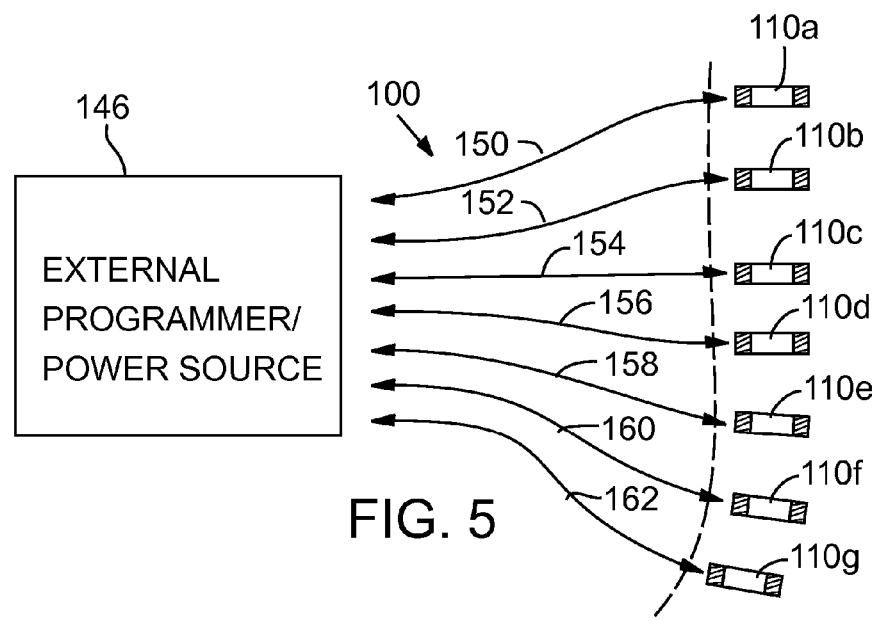
FIG. 5 is a schematic diagram illustrating a plurality of microstimulators communicatively coupled to an external programmer/power source.

The microstimulator 110 can include electrical circuitry for receiving power and/or data from an external transmitting source, such as an external programmer/power source 146 as illustrated in FIG. 5, placed outside of the body and providing inductive, radio-frequency (RF) or other electromagnetic coupling. For example, electrical circuitry includes an inductive coil for receiving power and RF data signals and an integrated circuit chip(s) for decoding and storing stimulation parameters and generating stimulation pulses (either continuous or intermittent) and additional discrete electrical components required to complete the electrical circuit functions such as resistor(s), coil(s), capacitor(s), diode(s) and the like.

In an example, the microstimulator 110 includes programmable memory allowing the stimulation and control parameters to be adjusted as a subject's condition changes without removing the microstimulators from the subject. In an additional example, sufficient voltage in the secondary coil within the microstimulator 110 is induced by using a Class E power transmitter, and highly resonant coils allow high currents to be sustained with minimal power consumption. In another example, 36 bits of data are utilized to command one stimulus pulse by one implanted microstimulator 110 (three 8-bit bytes plus formatting and parity information). These bits can be transmitted in 288 psec (about 3,400 commands per second). In a further example, the microstimulator 110 is a wireless injectable microstimulator such as a single-channel wireless injectable microstimulator.

The electrical circuitry of the microstimulator 110 can be encapsulated in a hermetically sealed package capsule 148. The capsule 148 may be made of numerous materials that can provide a hermetic barrier to the permeation of body fluids and water vapor into circuitry, but still permit the passage of electromagnetic fields used to transmit data and/or power. For example, the capsule 148 can be made of glass, ceramic, or other like biocompatible material. In an additional example, the capsule 148 is coated with a thermoplastic material such as polyethylene, polyester, polyurethane or a fluorinated carbon chain from the TEFLON® (TELFLON® is a registered trademark of DuPont, Wilmington, Del.) family to provide elasticity and thus, reinforcement to the capsule 148. In a further example, the coating is made from a liquid solution which is then applied to the microstimulator capsule via injection molding, dip-coating, or other like coating methods known in the art. The electrodes included within the electrical circuitry are allowed to remain partially exposed such as extending from the first end 142 and second end 144 of the microstimulator to provide electrical, stimulating pulses to a surrounding nerve or tissue.

An implantable microstimulator having the aforementioned properties is a BION® microstimulator that has been fully disclosed and described in U.S. Pat. Nos. 5,193,539, 5,193,540, 5,312,439, 5,324,316, and 5,405,367, each of which is incorporated by reference herein, in its entirety. BION® microstimulators are available from the Alfred E. Mann Foundation (AEMF) in Valencia, Calif., a not-for-profit medical research foundation dedicated to the research and development of advanced medical technologies. For example, a BION1 AMF microstimulator is a radio-frequency (RF) powered single-channel ceramic-cased implantable stimulator that can be implanted via a trocar-based insertion tool. The BION1 AMF microstimulator produces asymmetric biphasic constant-current pulses and incorporates an internal electrolytic capacitor to achieve charge balance through platinum-iridium electrodes. This microstimulator receives power as well as stimulation commands via a 2 MHz AC magnetic link from an external coil that is worn by a subject. For instance, one coil can control up to 255 uniquely addressable BION® microstimulators.

FIG. 5 provides an example of a plurality of injectable microstimulators remotely electronically coupled to an external programmer/power source 146. As illustrated in FIG. 5, a first microstimulator 110a is implanted adjacent to vertebral column 100 of a subject to provide stimulation to a first location. Additional microstimulators 110b, 110c, 110d, 110e, 110f and 110g are implanted on spinal nerves at adjacent descending spinal levels. Although the drawing illustrates implantation of the microelectrodes on only one spinal nerve at each level, the microelectrodes can be implanted on corresponding contralateral spinal nerves at each level. Each of the microstimulators provides electrical stimulation to a specific spinal location. The external programmer/power source 146 can control the operation of each of the implanted microstimulators and is capable of sending information such as commands and data to the microstimulator via an RF link, an ultrasonic link, a thermal link, or an optical link. In addition, the external programmer/power source 146 can receive information from the microstimulators. The external programmer/power source 146 can be programmed by a subject or a healthcare provider. In particular disclosed embodiments the programmer/power source provides a signal to each of the implanted microelectrodes to simultaneously stimulate each of the nerves in which they have been placed in stimulating relationship. Simultaneous (or near simultaneous) activation of each of the microelectrodes helps provide a coordinated contraction of the intercostals muscles to activate forced expiration (as in a cough).

However the plurality of injectable microstimulators can be independently programmable single-channel stimulators allowing each microstimulator to be programmed with at least one stimulation pattern. For example, the implanted microstimulators can operate independently or can operate in a coordinated manner with other similar implanted microstimulators, other implanted devices, or other devices external to the subject's body, as shown by the control lines 150, 152, 154, 156, 158, 160, 162, and 164 in FIG. 5.

FIGS. 6 and 7 provide examples of placement of multiple microstimulators in a canine subject 200 in order to generate an expiratory function such as a cough. In an example, as illustrated in FIG. 6, to generate an expiratory function, microstimulators are bilaterally positioned along a canine's vertebral column 202 and rib cage 204, between the ribs, at the T7-L1 vertebral levels. Each microstimulator 110 is positioned between two adjacent ribs and within about 3 cm externally (distally) of the corresponding neuroforamen from which the spinal nerve emerges. In the illustrated example, the microstimulators are placed near the inferior margin of each nerve, near where the intercostal nerve for each level would usually be found. In an additional example, each microstimulator 110 is positioned within about 8 cm externally of the neuroforamen. In a further example, each microstimulator 110 is positioned within about 1.5 cm externally of the neuroforamen. FIG. 7 provides another example in which eight pairs of microstimulators are positioned bilaterally in the intercostal spaces near the inferior border of the rib along the mid-axillary region at vertebral levels T7 through L1 of the canine subject 200.

Figure 8A:
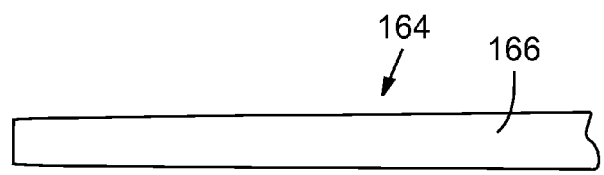
FIG. 8A is a fragmentary perspective view of an insertion tool for inserting a microstimulator into a subject.
Figure 8B:
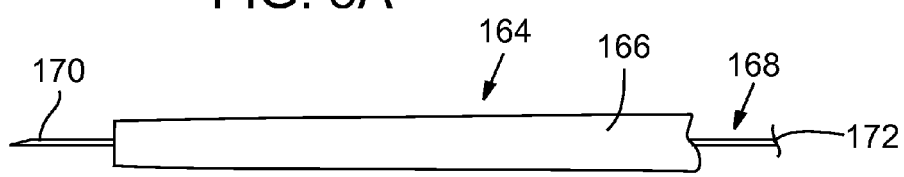
FIG. 8B is a perspective view of the insertion tool of FIG. 8A with an electrical stimulating probe extending through the lumen of the tool to locate the implant site for a micro stimulator.
Figure 8C:
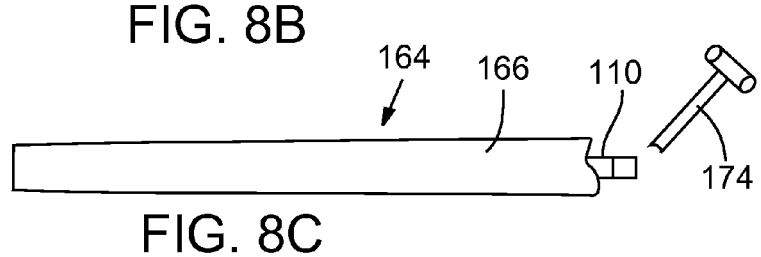
FIG. 8C is a perspective view of the insertion tool of FIG. 8A with a microstimulator inserted into the lumen of the tool to inject it into a subject.

FIGS. 8A-8C provide examples of an insertion tool 164 for positioning and inserting a microstimulator 110. The insertion tool 164 is of a size and a shape that allows minimally-invasive insertion of a microstimulator 110. In an example, the insertion tool 164 can include an external cannula 166 and a central trocar 168. The external cannula 166 can be formed of a material which provides sufficient rigidity to the tool to prevent bending of the insertion tool during use. Further, the lumen of the external cannula 166 can be coated or formed of a material such as a rigid, dielectric material which allows the microstimulator 110 to pass through the external cannula 166 without scratching the external surface of the microstimulator 110. The external cannula is of a diameter to allow a microstimulator 110 or a central trocar 168 to traverse the lumen of the cannula 166. For example, the internal lumen is generally cylindrical with a diameter capable of receiving a microstimulator 110 with a maximum diameter of approximately 2 to 2.4 mm or a 12-gauge trocar.

The central trocar 168 of the insertion tool 164 can be an electrically conductive probe including a first end 170 and a second end 172. In an example, the first end 170 of the probe is sharpened and positioned to extend beyond the external cannula 166. This configuration allows the central trocar 168 to be used to deliver current pulses to a desired site. Electrical stimuli can be delivered via the trocar 168 by connecting a conventional electrical stimulator to a connector located on the second end 172 of the central trocar 168.

When the desired position is reached, the electrical stimulation device is removed taking care not move the position of the external cannula 166. Once the electrical stimulating device is removed, a microstimulator 110 can be pushed through the lumen of the insertion tool by using a rod such as a blunt-ended push rod 174 as illustrated by FIG. 8C.

An insertion tool with the aforementioned properties is a BION® insertion tool available from the Alfred E. Mann Foundation (AEMF) in Valencia, Calif.

In a further example, an insertion tool includes a modified trocar needle substantially surrounded by a sheath such as a 12-gauge plastic sheath. The trocar needle includes a first end and a second end. The first end of the trocar needle is sharp and utilized to provide stimulation pulses to a nerve or tissue. The second end of the trocar needle includes a connector to facilitate coupling of the needle to a conventional laboratory stimulator.

Although the disclosed methods focus primarily on the use of microstimulators for stimulating an expiratory function in a subject with a spinal cord injury, it is contemplated that such methods may be used to stimulate an expiratory function in subjects with other neurological disorders such as traumatic brain injuries. In addition, these methods can be used in the post-operation or intensive care unit setting. For example, the disclosed methods can be employed to generate an expiratory function in a subject recovering from surgery.

The subject matter of the present disclosure is further illustrated by the following non-limiting Examples.

Example 1

Materials and Methods for Protocol I—Optimizing Placements and Stimulation Parameters for Microstimulators Animal preparation and surgical procedures. Nine male mongrel canines were used, each weighing between 25 and 35 kg. The canines were fasted overnight, with free access to water before surgery. Each canine was premedicated with 0.1 mg/kg acepromazine (administered via intramuscular injection (IM)), 25 mg/kg of sodium pentobarbital IM, followed by intubation with a cuffed endotracheal tube to maintain airway patency. Anesthesia was maintained by inhalation of isoflurane (1-2%). Controlled minute ventilation was initiated with a volume of 450 ml and a rate of 10-12 breaths/minute. Femoral venous and arterial lines were placed for intravenous access and blood pressure monitoring (P231 D; Gould-Statham, Oxnard, Calif.). Body temperature was maintained at 37±0.5° C. with a heating blanket. Tidal volume was recorded by electronic integration of the flow signal from a pneumotachograph system (Hans Rudolph RSS-100HR, Kansas City, Mo.). Tidal volume was measured to determine if adequate ventilation was achieved using the magnetic stimulator. End-tidal $PCO_2$ was monitored at the tracheal opening with a rapidly responding $CO_2$ analyzer (O. R. SARA; PPG Biomedical System, Lenexa, Kans.). Tracheal pressure was recorded with a differential pressure transducer (Validyne MP-45, Validyne, Northridge, Calif.). The catheter placed in the femoral vein was used for administration of intravenous fluids and medication, as needed.

Laminectomy and spinal cord transection. A thoracic laminectomy was performed on each canine, and was followed by spinal cord transection at T2. T2 transection was performed to eliminate any expiratory muscle input from lower intercostals nerves. An incision in the skin was made at the T1-T4 level and the muscle layers were separated until the posterior vertebral body of T3 was completely exposed. After removal of the spinal process and lamina of the T3 vertebra, the spinal cord was exposed over a 2.5-3.0 cm range at the level of T2-T3. The spinal cord was ligated proximally and distally with a 2 cm separation between the ligations. The section of the spinal cord between the two ligations was completely removed, and the incision of the muscles and skin were then separately closed by suture.

Implantation of microstimulators. Prior to the implantation of the microstimulators, a commercially available battery-powered electrical stimulation device (ESD) with a percutaneous stimulation probe and a trocar-based implant tool were used to identify the locations along the intercostal nerves. Three anatomical placements were used for comparison for microstimulator implantation: proximal placement, 1 to 3 cm distal to the neuroforamen; medial placement, along the mid-axillary line; and distal placement, being placed in the abdominal musculature.

A. Proximal placement of the microstimulators. While the animal was prone, a vertical incision of approximately 1 to 1.5 cm in length at the spinous process region was made and the stimulating probe of ESD was introduced through the paraspinal muscles with an introducer. Initially the probe was positioned approximately 3 cm lateral to the spinous process between two adjacent ribs, as close to the neuroforamen as possible. The probe was then moved slightly in all directions, and followed by a short burst of stimuli at each adjustment. The final position was determined where the strongest muscle contraction was detected. After locating this site, the probe was withdrawn while the introducer remained in the same position and then one microstimulator was inserted through the introducer into the same site where the head of the probe was. Again, slight adjustments of microstimulator position were made to obtain the optimal muscle contractions. The same procedures were repeated from T7 to L1 bilaterally. The proximal placements of T7-L1 were then studied with stimulation of a single pair to eight pairs of microstimulators to obtain maximal expired pressure, by which the optimal number of microstimulators were determined. After the completion of the study of proximal placement, eight microstimulators were removed to be used for the median placement protocol.

B. Median placement of the microstimulators. Vertical incisions similar to those used in the proximal placement studies were made along the mid-axillary region bilaterally. Further, following the same procedures as described above, eight microstimulators were placed in the intercostal spaces on each side at levels between T7 and L1.

C. Distal placement of the microstimulators. The animal was placed supine and eight microstimulators were inserted directly into the abdominal muscles near the motor points for the distal placement protocol. A similar insertion optimization protocol was used to determine maximum abdominal muscle contraction.

Stimulation protocols. The stimulation parameters were set at 20 Hz, 2 second burst length, and the intensity was gradually increased from about 4 mA, until reaching supramaximal stimulation. Changes in airway pressure were recorded and measured in response to each stimulation. After each microstimulator was inserted, the microstimulator was tested individually to verify that it was functioning appropriately. This was followed by stimulation of pairs: T7 right and left, T8 right and left, etc., and then by groupings with two pairs (T7-T8, T8-T9, T9-T10, T10-T11, T11-T12, T12-T13, T13-L1), three pairs (T7-T9, T8-T10, T9-T11, T1-T12, T11-T13, T12-L1), four pairs (T7-T10, T8-T11, T9-T12, T10-T13, T1-L1), five pairs (T7-T11, T8-T12, T9-T13, T1-L1), six pairs (T7-T12, T8-T13, T9-L1), seven pairs (T7-T13, T8-L1), and eight pairs (T7-L1).

Monitoring parameters. Throughout the present studies, the blood pressure and heart rate were recorded from an arterial line. The airway flow and tracheal pressure were also monitored.

Evaluation of muscle fatigue. Skeletal muscle fatigue may occur at the level of the central nervous system (central failure), at the neuromuscular junction and/or plasmalemma failure, during excitation-contraction coupling, and at the myofibrillar level. The fatigue of expiratory muscle secondary to FES or microstimulation was assessed both from changes in the maximal static expiratory pressure and in the centroid frequency of the abdominal muscle electromyogram (EMG; Suzuki et al., *Nihon Kyobu Shikkan Gakkai Zasshi* 30(4): 547-531, 1992). For microstimulation studies, the maximal expired pressured ($P_{max}$) was obtained by gradually increasing the intensity of stimulation. Further, the following stimulation parameters were employed: stimulation frequency—20 Hz; stimulation burst length—2 seconds; duty cycle—0.5; expiratory rate—15/minute; duration of stimulation—30 minutes; expiratory loading—50% of the $P_{max}$. A modified tension-time index (TTi) was calculated as the ratio of expired pressure (P) generated after 30 minutes of stimulation to $P_{max}$, respectively. The modified formula, $TT_i = T_i/T_{tot} \times P/P_{max}$, was used to evaluate expiratory muscle fatigue based upon a study on the diaphragm fatigue (Bellemare et al., *J. Appl. Physiol.* 54(6): 1597-606, 1983). According to the formula, $T_i$ is the time of contraction during an inspiratory cycle, $T_{tot}$ is total cycle duration (inspiratory+expiratory time), and $T_i/T_{tot}$ is breathing duty cycle. For the following studies, $T_i$ referred to the expiratory cycle, or the duration for expiratory muscle stimulation. Further, $T_i/T_{tot}$ referred to the expiratory duty cycle. The EMG activity of the intercostal muscle and external oblique muscle was recorded. The digitized EMG signals were analyzed by a fast Fourier transformer. The centroid frequency ($f_c$) was obtained according to Sieck et al. (*Respir. Physiol.* 61(2): 137-52, 1985). The $f_c$ was expressed as a percentage of the average value of the first five stimulation burst. The $f_c$ obtained at the end of the 30 minutes of stimulation was compared with the baseline $f_c$.

Statistical methods. The changes in $P_{aw}$ obtained from the study were expressed as mean±standard error of the mean (SEM). Statistical analyses were performed using a two samples student t-test; a p-value of <0.05 was considered significant.

Example 2

Proximal Placement Stimulation Protocols

This example demonstrates that maximum $P_{aw}$ generation occurs when at least seven pairs of microstimulators are placed proximally in the lower thoracic levels of the canine.

Figure 9:
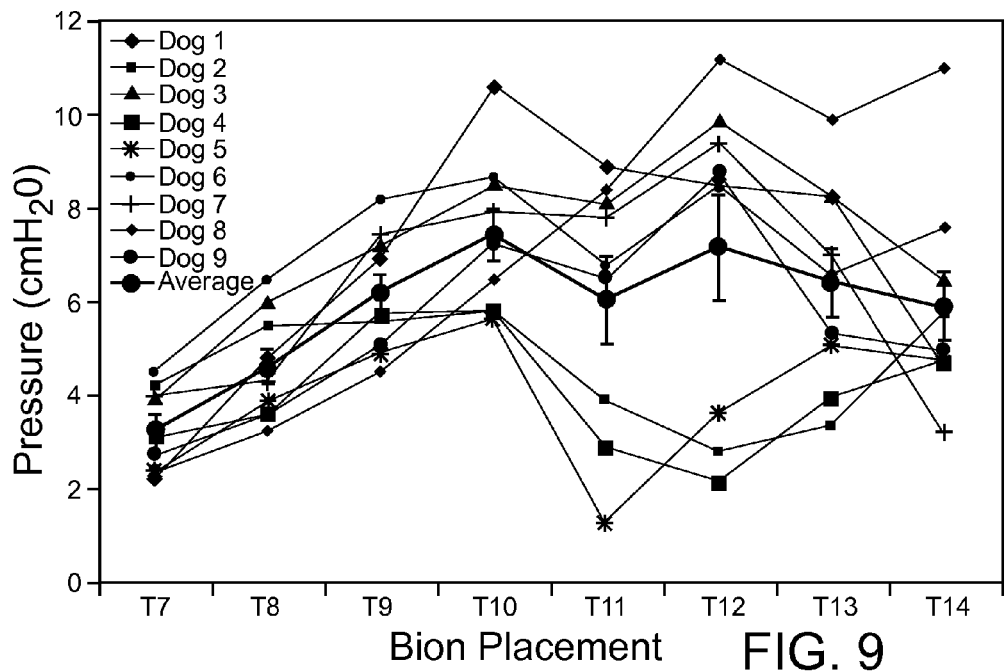
FIG. 9 is a graph illustrating the effects of single level spinal nerve stimulation on airway pressure by microstimulators positioned in the lower thoracic region of a canine.

The effects of single level spinal nerve stimulation using microstimulators in the lower thoracic levels from T7 to L1 are shown in FIG. 9. Stimulation parameters were set at 20 Hz, 2-second burst length, and 8.1 mA intensity. There was no observable muscle contraction of the limbs or contraction of the upper rib cage muscles during this protocol. As shown in FIG. 9, stimulations applied at spinal cord levels between T10 and T12 provided maximal changes in $P_{aw}$ of 7.4±0.6, and 7.2±1.1 cmH$_2$O, respectively. Single level stimulation at T9, T11, T13, and L1 resulted in less $P_{aw}$ changes than that of T10 or T12 (p>0.05), while stimulations at T7 and T8 only produced 3.3±0.3 and 4.6±0.4 cmH$_2$O of $P_{aw}$, respectively, p<0.05. For each animal, $P_{aw}$ gradually increased as the level of stimulation changed from T7 to T10, Substantial disparity occurred at levels below T11 (FIG. 9).

Figure 10:
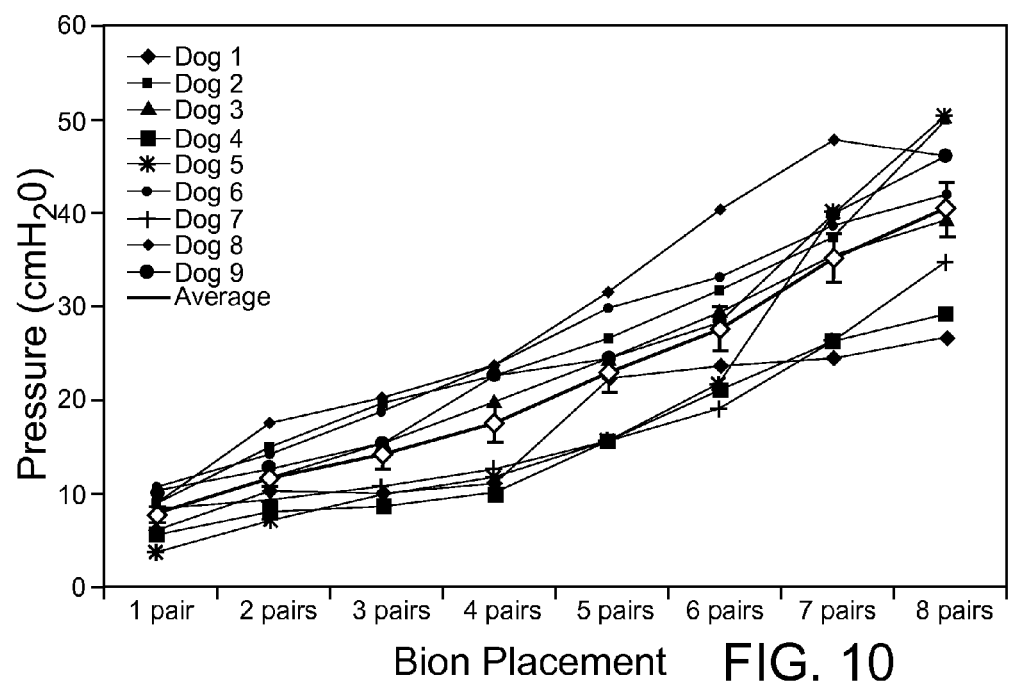
FIG. 10 is a graph demonstrating that changes in airway pressure are affected by the number of microstimulator pairs utilized to bilaterally stimulate spinal nerves in the lower thoracic region of a canine.

Maximal mean $P_{aw}$ generations using one to eight levels of spinal nerve stimulation simultaneously are shown in FIG. 10, these are 8.4±0.8 (one level), 12.2±1.0 (two levels), 14.6±1.4 (three levels), 17.8±1.8 (four levels), 23.0±1.8 (five levels), 27.7±2.2 (six levels), 35.2±2.7 (seven levels), and 40.4±2.9 (eight levels) cmH$_2$O, respectively. These values were the largest $P_{aw}$ generated among different combination of spinal nerve pairs in perspective levels of spinal nerve stimulation. The stimulation parameters were also set at 20 Hz and 2 second burst length, with varying stimulation intensity from 3.78 to 10.8 mA. These results show that stimulation of six or less pairs of spinal nerves produced significantly lower $P_{aw}$ than that of seven or eight pairs, p<0.05.

As illustrated in FIG. 10, the correlation between the $P_{aw}$ generation and the number of microstimulators is virtually linear. The $P_{aw}$ peaked at 35.2±2.7 cmH$_2$O with seven pairs of microstimulators, not significantly differently from 40.4±2.9 cmH$_2$O with eight pairs. This number is about 92% of 44±4 cmH$_2$O obtained from FES lower thoracic ventral root stimulation with the electrode placed at T9-T10, which technique was demonstrated to activate all major expiratory muscles, including abdominal muscles and internal intercostals muscles. This indicates that in order to generate maximal $P_{aw}$ at least seven pairs of microstimulators are needed.

Figure 11:
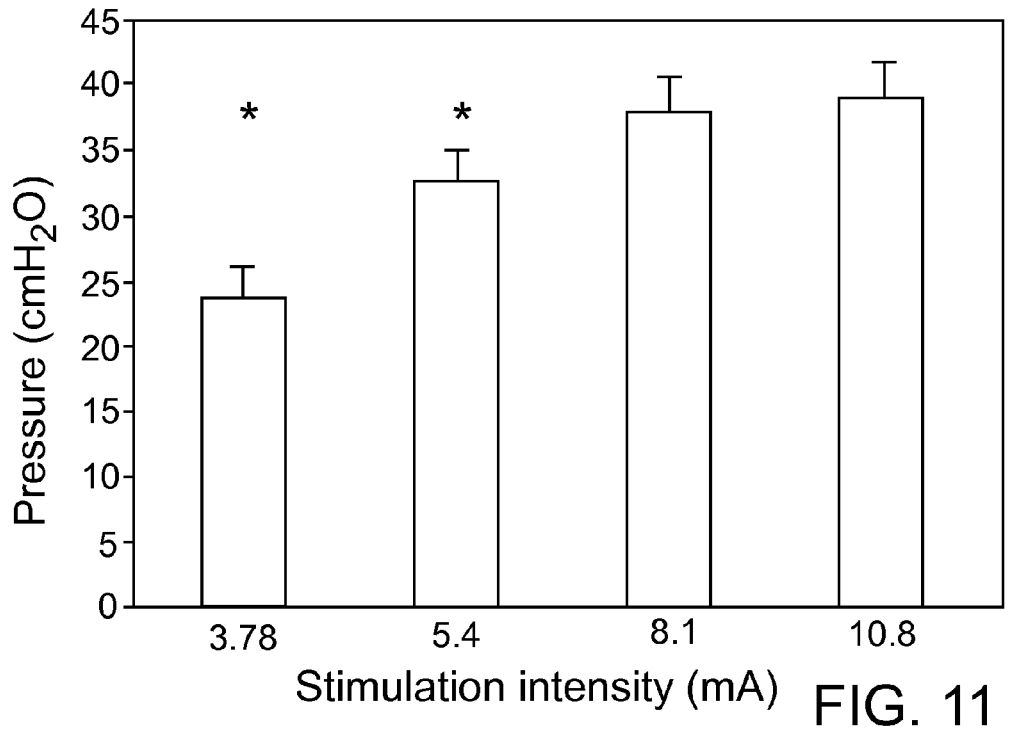
FIG. 11 is a graph depicting the changes in airway pressures from stimulating different combinations of four consecutive spinal nerves in a canine.

The effect of stimulus intensity (0.2 ms pulse width) on airway pressure generation at FRC using eight pairs of spinal nerves is displayed in FIG. 11. Increasing stimulus intensity at a constant frequency (20 Hz) resulted in a progressive increase in airway pressure generation until a plateau was reached at about 8.1 to 10.8 mA. Repeated stimulation at higher intensity showed no significant increases in airway pressure.

Figure 12:
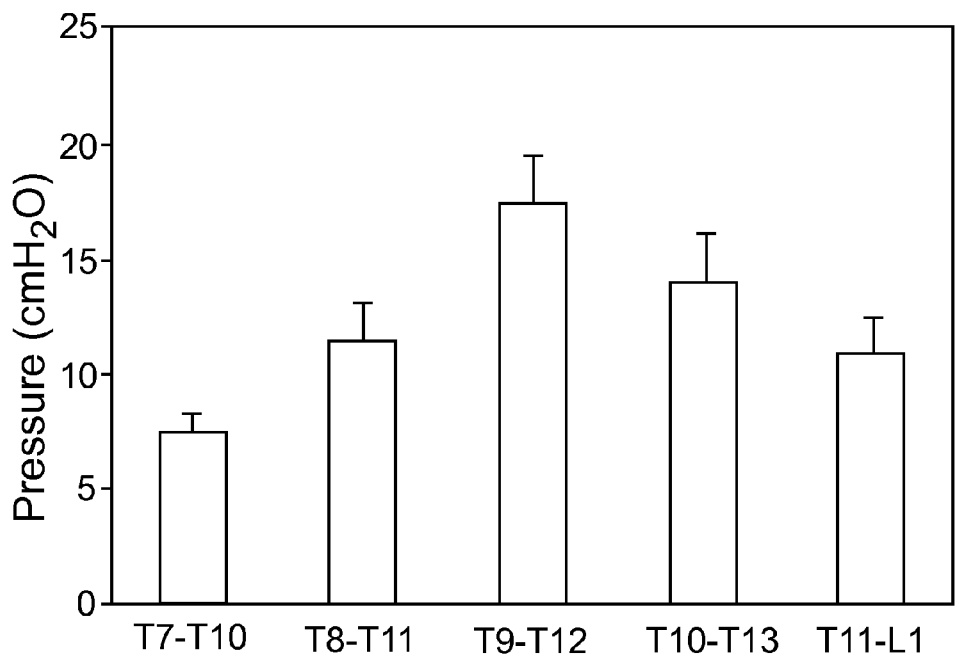
FIG. 12 is a graph illustrating the intensity profile of airway pressure generation caused by stimulating eight pairs of spinal nerves between T7-L1 vertebral levels in a canine.

As was indicated from single level spinal nerve stimulation proximally, multiple levels of spinal nerve stimulation involving T9-T12 produced higher $P_{aw}$ than stimulations that did not involve T9-T12. For example, as illustrated in FIG. 12, $P_{aw}$ generation increased as the stimulation current increased until 8.1 mA. In the case of four level spinal nerve stimulation at different spinal nerve levels, the highest maximal mean $P_{aw}$ was 17.8±1.8 cmH$_2$O at T9-T12. Repeated stimulation at higher amplitudes failed to produce higher pressure. Further, the results were similar when the order of stimulation currents (higher stimuli first) was reversed after the subjects had sufficient rest.

Thus, with proximally placed microstimulators maximal, $P_{aw}$ is generated by using at least seven pairs of microstimulators in which four of the pairs of microstimulators are positioned adjacent to T9-T12 vertebrae.

Example 3

Median and Distal Placement Stimulation Protocols

This example demonstrates that median and distal placement of microstimulators produced three times or almost six times less $P_{aw}$ than those generated with proximally placed micro stimulators.

Figure 13:
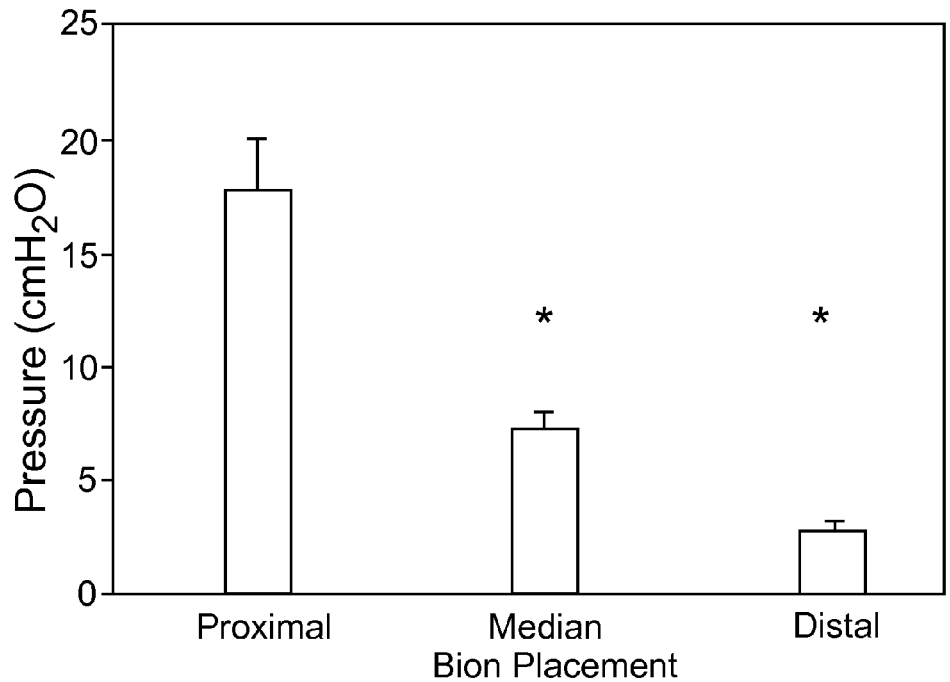
FIG. 13 is a graph illustrating that changes in airway pressure by stimulation of four spinal nerve levels are affected by the position of the microstimulators.

Alternative placements for the microstimulators that would produce comparable results to those found with the proximal placement were explored. Median placement involved the positioning of microstimulators midway along the intercostal nerves and distal placement involved direct abdominal muscle stimulation. These placements were studied with each placement having four pairs of microstimulators inserted bilaterally at T9, T10, T11, and T12. Median placement (at the mid-axillary region) of four-level spinal nerve stimulation (T9 to T12) produced 7.2±0.8 cmH$_2$O (FIG. 13), which was 41% of the $P_{aw}$ generated by proximal stimulation at T9-T12. Using direct implantation of microstimulators in the abdominal muscles (distal placement) produced 2.5±0.38 cmH$_2$O. This value was 15% of the $P_{aw}$ generated by proximal placement stimulation at T9-T12.

Therefore, the proximal placement of microstimulators produced higher $P_{aw}$, almost 3 times more than those of the median placement and almost 6 times more than those of the distal placement.

Example 4

Materials and Methods for Protocol II—Comparing Microstimulation with other Neuromuscular Stimulation Techniques Animal Preparation. Twenty-four canines were prepared, anesthetized, and intubated as described in Example 1, Animal Preparation and Surgical Procedures. After the spinal cord transaction at the T2 level, the skin area for electrode placements was shaved. The canines were divided into three sets: eight of the 24 canines were used for BION® implantation; eight of the 24 canines were used for FES studies; and eight of the 24 canines were used for FMS studies. Animals were euthanized after the experiments with intravenous Euthasol at a dosage of 1 ml/5 kg. When necessary, the experiments were ended at the point at which an increased partial pressure of arterial CO$_2$ ($P_aCO_2$) had doubled or when the systolic blood pressure decreased by more than 40 mmHg from baseline values. Tidal volume was recorded by electric integration of the flow signal from a pneumotachograph (Fleish no. 1). Tracheal pressure was measured with a separate differential pressure transducer (Validyne Mp 45).

Placement of BION® stimulators. Similar procedures to those described in Example 1, A. Proximal placement of the microstimulator were utilized for BION® stimulator placement. The BION®s were injected sequentially by an insertion tool into the optimal placements that were identified in Example 2.

FES of ventral roots. A multi-contact disk stimulating electrode including eight leads was inserted epidurally on the T8-T10 ventral surface of the spinal cord via a T4-T5 laminectomy, and then advanced caudally to the lower thoracic spinal cord near T8-10. The electrode leads were 4 mm in diameter embedded in polyurethane plastic and positioned 20 mm apart. Precise position of each electrode in relation to specific spinal roots was determined in each animal postmortem. All incisions were sutured after electrode placement.

FES of abdominal muscles. Six disk surface electrodes (three pairs) having a diameter of 2.5 cm were bilaterally placed on the surface of the external oblique muscles near the motor points between the costal margin and pelvis for direct muscle stimulation.

FMS. A commercially available magnetic stimulator was used to generate the magnetic field. The center of the magnetic coil was placed at T6, T7, T8, T9, T10, T11, and T12 for maximal expiratory stimulation.

Stimulation protocol for BION® stimulators. Individual bionic stimulation was tested first to see if the BION® was functioning properly. The same procedure as outlined in Section III., Example 1, Stimulation protocols was followed to determine optimal BION® placement(s) and the optimal number of BION®s to be used.

Stimulation protocol for FES. The stimulation protocol for FES of ventral spinal roots were similar to the procedures described for BION® equivalent electrodes detailed in Example 1, Stimulation protocols. The stimulation parameters started at 20 Hz, 2-second burst length, and the intensity gradually increased to obtain supramaximal stimulation. Supramaximal stimulation was defined as the stimulus amplitudes and frequencies that resulted in maximal inspired volume.

Stimulation protocol for FMS. The stimulation parameters that produce maximal expired pressure by FMS were determined in the following manner. A stimulation parameter of 60%, 20 Hz, and 2-second pulse train were used at the optimal stimulation site. Intensity was gradually increased from 60% to 100% while keeping the frequency at 20 Hz.

Monitoring parameters. Throughout the entire study, the EKG, blood pressure and heart rate were recorded from the arterial line. Tidal volume was recorded by electric integration of the flow signal from a pneumotachograph (Fleish no. 1). Tracheal pressure was measured with a separate differential pressure transducer. EMG and muscle contraction was measured as described Example 1, Evaluation of muscle fatigue.

Evaluation of muscle fatigue of BION® stimulation. Expiratory muscle fatigue for BION® stimulation was evaluated as described in Example 1, Evaluation of muscle fatigue.

Example 5

FES of the Ventral Root in T2 Transected Canines

This example demonstrates that maximum airway pressure is generated by FES of the ventral root in T2 transected canines by using stimulation parameters including a frequency of 50 Hz and an intensity of 60 V to stimulate T9.

Figure 14:
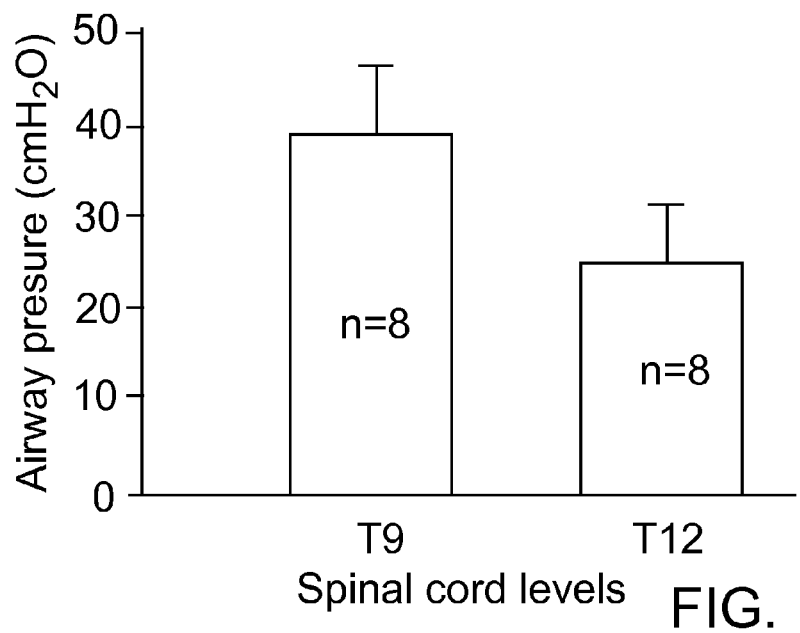
FIG. 14 is a graph illustrating airway pressure generated by FES of the ventral root at T9 and T12 in T2 transected canines.

To determine if the amount of airway pressure generated by FES of the ventral root was dependent upon the level of the lower thoracic region at which stimulation occurs, FES of the ventral root was used to stimulate T9 and T12. Stimulation parameters were set at a frequency of 50 Hz and an intensity of 60 V. As illustrated in FIG. 14, airway pressure was significantly greater when stimulation occurred at the level of T9 compared to T12.

Figure 15:
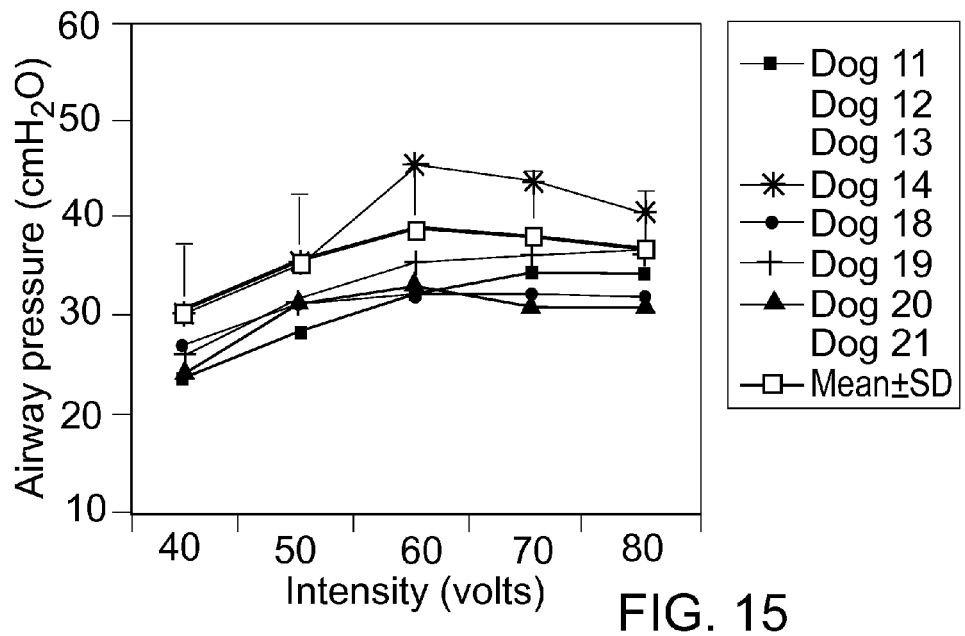
FIG. 15 is a graph illustrating airway pressure generated by FES of the ventral root at vertebral level T9 with varying electrical intensity (volts) at a frequency of 50 Hz in T2 transected canines.

In addition, FIG. 15 demonstrates that the amount of airway pressure generated by FES of the ventral root at vertebral level T9 in T2 transected canines is dependent upon the intensity of the stimulation. Frequency was held constant at 50 Hz while the intensity of the stimulation ranged from 40 V to 80 V. As illustrated in FIG. 15, maximum airway pressure was reached by stimulating with an intensity of 60 V (n=8). Further, stimulation with intensities greater than 60 V resulted in slight reductions in airway pressure. Thus, maximal airway pressure by FES-ventral root stimulation at vertebral level T9 in T2 transected dogs was generated by stimulating with an intensity of 60 V.

Figure 16:
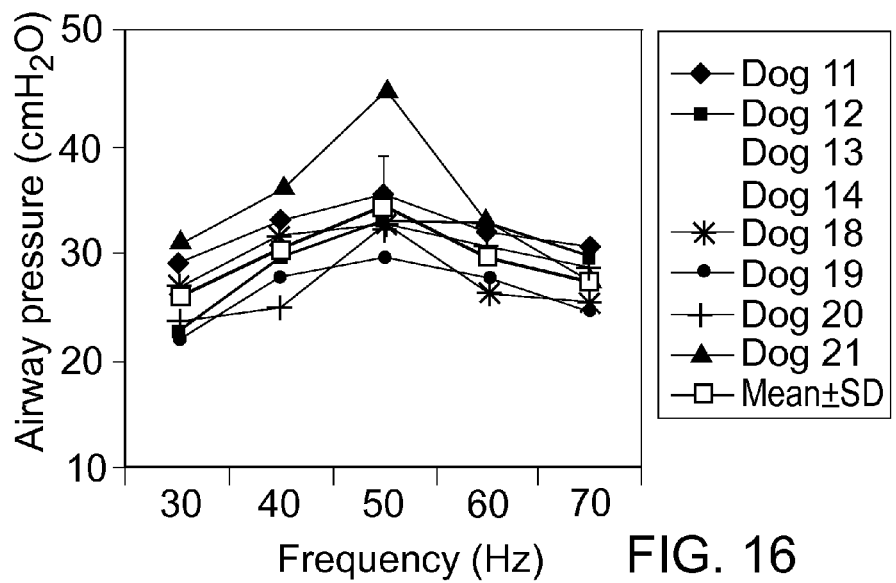
FIG. 16 is a graph illustrating airway pressure generated by FES of the ventral root at vertebral level T9 with varying frequencies of electrical current at an intensity of 60 V in T2 transected canines.

Further, FIG. 16 establishes that the amount of airway pressure generated by FES of the ventral root at T9 in T2 transected dogs is also dependent upon stimulation frequency. Stimulation intensity was held constant at 60 V while frequency of stimulation ranged from 30 Hz to 70 Hz. As illustrated in FIG. 16, maximum airway pressure was generated by stimulating with 50 Hz (n=8). Stimulation with frequencies greater than 50 Hz such as 60 Hz or 70 Hz resulted in a reduced airway pressure.

Thus, maximum airway pressure was generated by FES of the ventral root in T2 transected canines by using stimulation parameters including a frequency of 50 Hz and an intensity of 60 V to stimulate vertebral level T9.

Example 6

FES of the Abdominal Muscles in T2 Transected Canines

This example demonstrates that maximum airway pressure is generated by FES of the abdominal muscles in T2 transected canines by using stimulation parameters including a frequency of 50 Hz and an intensity of 150 V.

Figure 17:
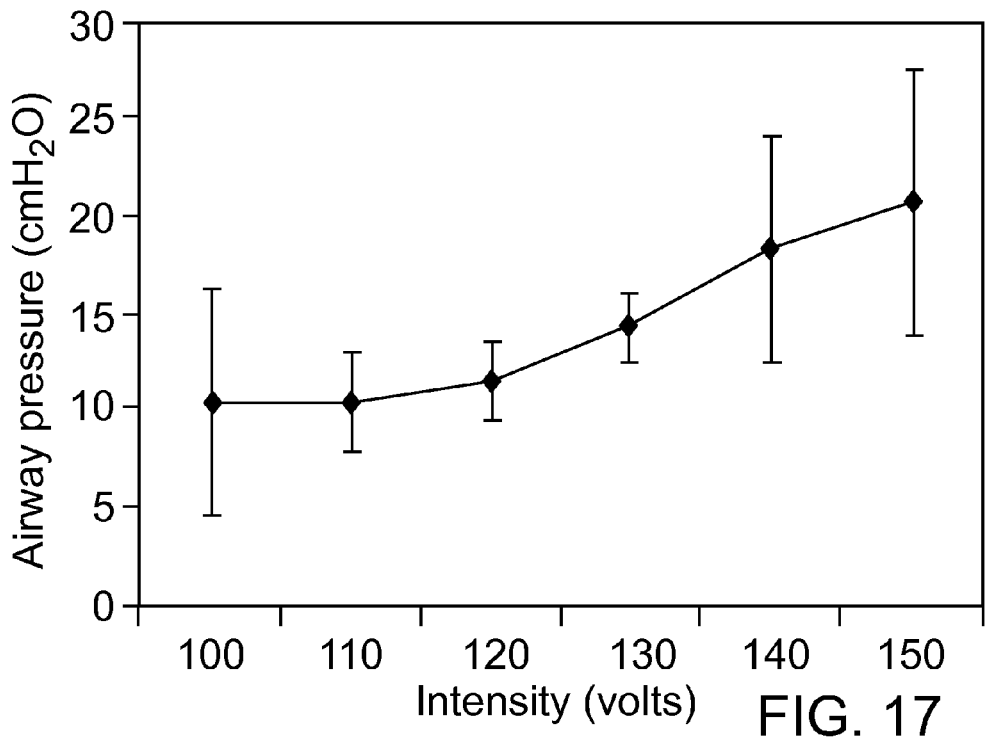
FIG. 17 is a graph illustrating airway pressure generated by FES of abdominal muscles at different electrical intensities (volts) with a constant frequency (50 Hz) in T2 transected canines.
Figure 18:
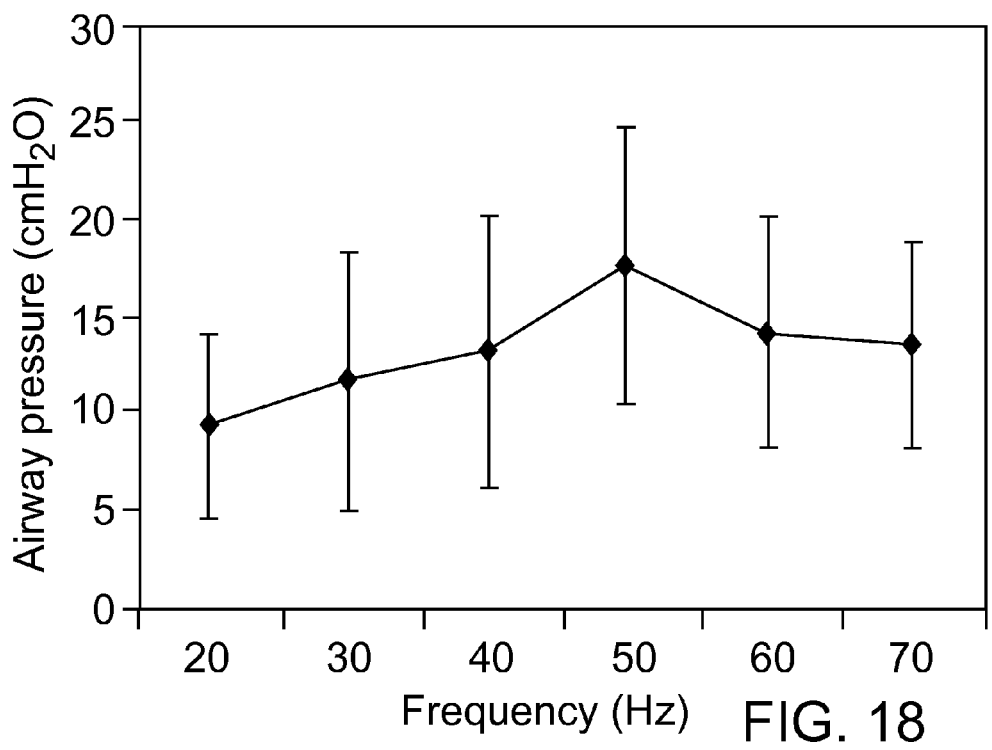
FIG. 18 is a graph illustrating airway pressure generated by FES of abdominal muscles in canines at different electrical frequencies with a constant intensity (150 V).

To determine the optimal stimulation parameters for airway pressure generated by FES of the abdominal muscles, frequency was first held constant at 50 Hz while the intensity of the stimulation ranged from 100 V to 150 V. As illustrated in FIG. 17, maximum airway pressure was reached by stimulating with a stimulation intensity of 150 V. Next, stimulation intensity was held constant at 150 V while frequency of stimulation ranged from 30 Hz to 70 Hz. As illustrated in FIG. 18, maximum airway pressure was generated by stimulating with 50 Hz (n=8). Stimulation with frequencies greater than 50 Hz such as 60 Hz or 70 Hz resulted in a reduced airway pressure.

Thus, maximum airway pressure was generated by FES of the abdominal muscles in T2 transected canines by using stimulation parameters including a frequency of 50 Hz and an intensity of 150 V.

Example 7

FMS of the Lower Thoracic Nerves in T2 Transected Canines

This example demonstrates that maximum airway pressure is generated by FMS of the lower thoracic region T12 in T2 transected canines by using stimulation parameters including a frequency of 50 Hz and an intensity of 80%.

Figure 19:
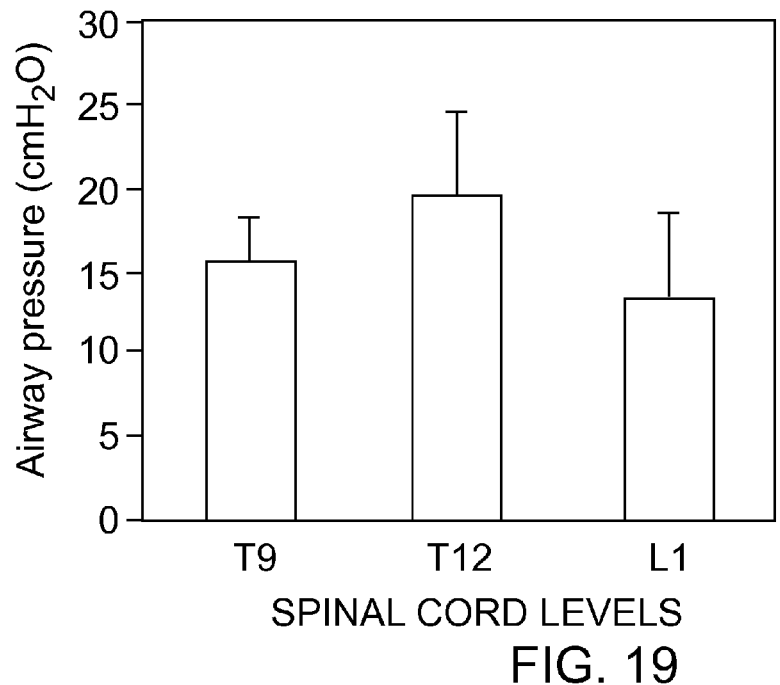
FIG. 19 is a graph illustrating airway pressure generated by FMS at vertebral levels T9, T12, and L1 in T2 transected canines.

To determine if the amount of airway pressure generated by FMS of the lower thoracic nerves was dependent upon the level of the lower thoracic region at which stimulation occurs, FMS was used to stimulate T9, T12 and L1 regions. Stimulation parameters were set at a frequency of 20 Hz and an intensity of 80%. As illustrated in FIG. 19, airway pressure was significantly greater when stimulation occurred at the level of T12 compared to T9 or L1 regions.

Figure 20:
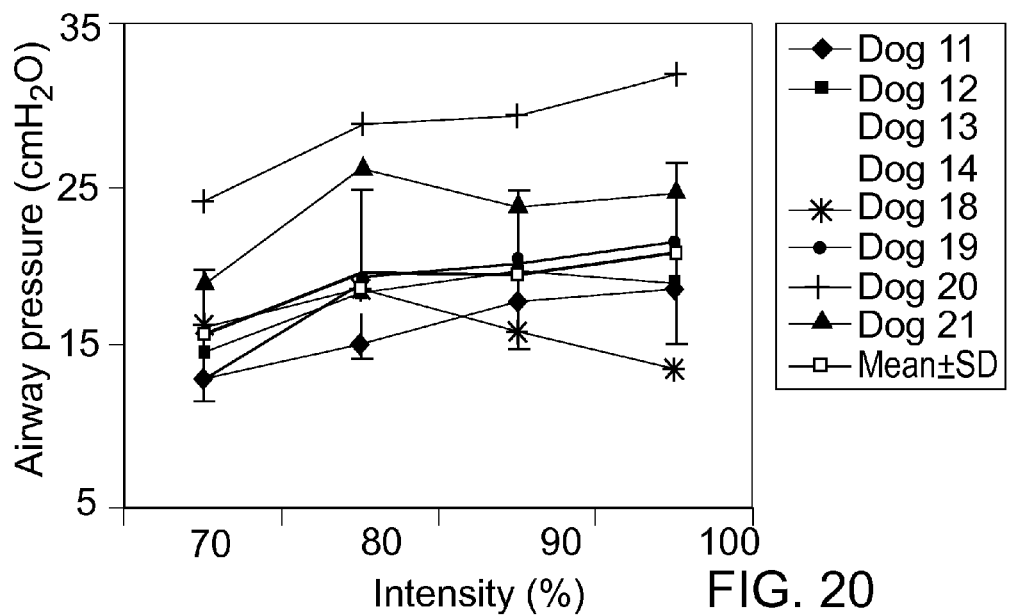
FIG. 20 is a graph illustrating airway pressure generated by FMS with a constant frequency (50 Hz) in T2 transected canines.

To determine the optimal stimulation parameters for airway pressure generated by FMS, frequency was first held constant at 20 Hz while the intensity of the stimulation ranged from 70% to 100%. As illustrated in FIG. 20, maximum airway pressure was reached by stimulating with a stimulation intensity of 80%. Stimulation with intensities greater than 80% such as 90% or 100% had no significant effect on airway pressure. For example, in one animal, a slight increase in airway pressure was noted with the greater than 80% stimulation intensity (see, for example, Dog 20). In another study, a slight decrease in airway pressure was noted with the greater than 80% stimulation intensity (see, for example, Dog 18).

Thus, maximum airway pressure was generated by FMS of T12 in T2 transected canines by using stimulation parameters including a frequency of 20 Hz and an intensity of 80%.

Example 8

Comparison of Maximum Airway Pressures Generated using Microstimulators, FES-Ventral Root Stimulation, FES Abdominal Muscle Stimulation, and FMS Lower Thoracic Nerve Stimulation This example demonstrates that transcutaneously placed, remotely activated and operated microstimulators generate equivalent maximum airway pressures as FES of the ventral root, while avoiding many of the clinical drawbacks of surgically implanted FES electrodes.

The maximum airway pressures were generated using BION®s, FES-ventral root stimulation, FES abdominal muscle stimulation, and FMS lower thoracic nerve stimulation. Stimulation parameters for FES of the ventral root with a multi-contact disk stimulating electrode including eight leads positioned at T9 included a stimulation frequency of 50 Hz and intensity of 60 V. FES of the abdominal muscles included a stimulation frequency of 50 Hz and stimulation intensity of 150 V. FMS of T12 region included a stimulation frequency of 20 Hz and stimulation intensity of 100%. BION® stimulation included use of eight pair of stimulators with a frequency of 20 Hz and a stimulation frequency of 8.1 mA.

Figure 21:
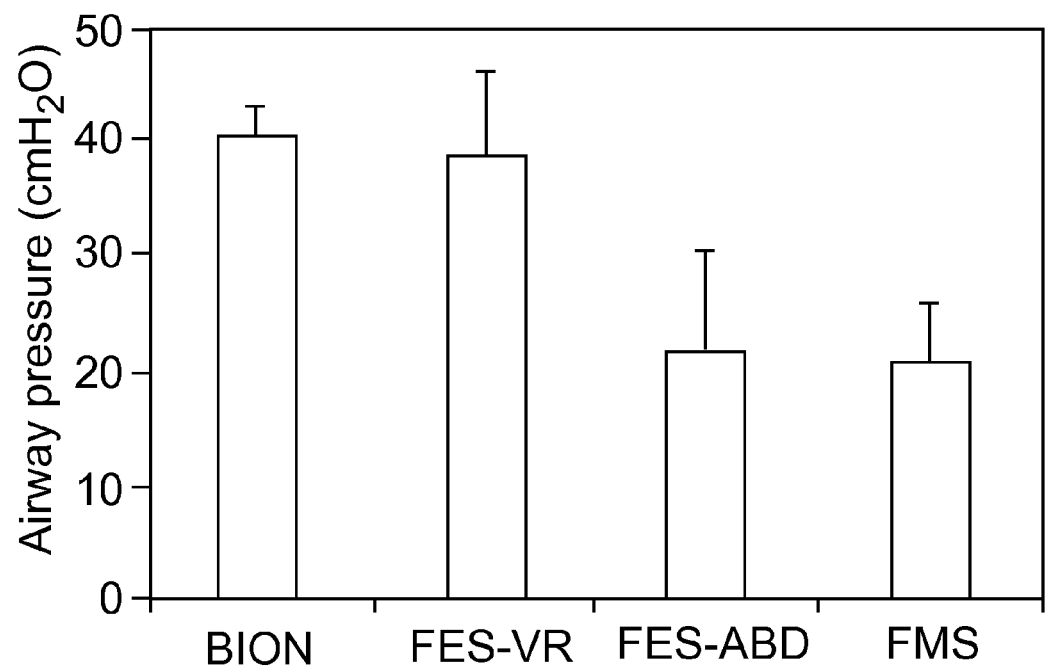
FIG. 21 is a graph comparing the maximum airway pressures generated using microstimulators (BION®; BION is a registered trademark of Advanced Bionics Corporation, Valencia, Calif.), FES-ventral root stimulation, FES-abdominal muscle stimulation, and FMS lower thoracic nerve stimulation.

As illustrated in FIG. 21, maximum airway pressure was reached by stimulating with either BION® stimulation (40.4 cmH$_2$O) or with FES of the ventral root at T9 (39.05 cmH$_2$O). BION® stimulation or FES of the ventral root at T9 resulted in significantly greater maximum airway pressure when compared to airway pressure generated with FES of abdominal muscles (18.03 cmH$_2$O) or FMS of the T12 region (21.06 cmH$_2$O).

Thus, expired neuromuscular stimulation using microstimulators such as BION®s is a viable alternative to generate similar airway pressures as FES of the ventral root. The use of microstimulators is desirable over FES because microstimulator implantation is minimally invasive compared to FES of the ventral root which requires major surgery. Further, the risk of infection is reduced with the use of microstimulator compared to FES.

Example 9

Method of Stimulating an Expiratory Function in a Human

According to the teachings herein, one can stimulate an expiratory function in a human with a respiratory dysfunction such as that caused by an SCI by implanting a microstimulator adjacent at least one thoracic spinal nerve that innervates an intercostal muscle and applying a stimulating electrical current from the microstimulator to the thoracic spinal nerve at a sufficient intensity and duration to induce a forced contraction of the intercostal muscle innervated by that spinal nerve. In an example, a subject with respiratory dysfunction is identified. For instance, a subject with impaired respiratory function from a SCI occurring at vertebral level T2 is incapable of producing an effective expiratory function such as a cough to remove airway secretions.

Alternatively a subject with a neuromuscular disorder that affects respiratory function is selected for treatment. Examples of such subjects would be those with an idiopathic disorder such as Guillain-Barre syndrome, an infectious disorder such as poliovirus infection, or a degenerative disorder such as amyotrophic lateral sclerosis.

Following subject selection, the optimal placement of each microstimulator can be determined as outlined in Example 1, Stimulation parameters. For example, an insertion tool through which an electrical stimulating probe is advanced is used to locate an optimal implantation position of a first microstimulator adjacent a thoracic spinal nerve that innervates the intercostal muscle at the T7 region. An incision of approximately 1 to 1.5 cm in length at the spinous process region can be made to allow insertion of the instrument and electrical stimulating probe. The electrical stimulating probe is inserted into the lumen of the insertion tool about 3-5 cm lateral to a spinous process, and introduced through the paraspinal muscles to the possible implantation site adjacent thoracic spinal nerve in the T7 region. Initially the probe is positioned approximately 1-8 cm externally of the neuroforamen through which the spinal nerve emerges from the thoracic vertebra T7. The probe can be adjusted slightly until the optimal position is achieved. Each adjustment is followed by a short burst of stimuli to determine the effect of the adjustment on intercostal muscle contraction. The final/optimal position is denoted as the site at which the strongest muscle contraction occurs. After locating the implantation site, the probe is withdrawn from the lumen of the insertion tool taking care not to alter the position of the insertion tool. A microstimulator is then implanted by inserting the microstimulator into the lumen of the insertion tool and positioning the microstimulator into the site that the electrical stimulating probe tip occupied. Again, slight adjustments to the microstimulator's position can be made to obtain the optimal muscle contractions. The same procedure is then repeated for the implantation of additional microstimulators. For example, seven pairs of microstimulators can be positioned between T7 to L1 bilaterally. The placements of microstimulators in T6-L1 or T7-L2 regions can be achieved with stimulation of a single pair to eight pairs of microstimulators to obtain maximal expired pressure. An optimal number of microstimulators can be determined on a case by case basis, depending on the condition and needs of the subject.

It is contemplated that the number of microstimulators necessary to produce an expiratory function such as a cough may depend upon the cause of the respiratory dysfunction. For example, a SCI at vertebral level T2 may require seven to eight pairs of microstimulators in order to effectively clear airway secretions in a human. However, a SCI at vertebral level T10 may require less than seven to eight pairs because levels of injury from T12 through T5 are associated with a progressive loss of forceful expiration and cough compared to levels of injury from T5 through T1 in which all voluntary intercostal muscle function is lost. It is further contemplated that respiratory dysfunction caused by other injuries or diseases in addition to SCI may benefit from the use of microstimulators to assist subjects unable to effectively clear airway secretions.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method of inducing forced expiration in a subject, comprising:
    percutaneously placing an injectable microstimulator adjacent at least one thoracic spinal nerve that innervates an intercostal muscle, wherein the injectable microstimulator is placed within 8 cm externally of a neuroforamen through which the spinal nerve emerges from a thoracic vertebra, wherein percutaneously placing the injectable microstimulator comprises placing a first and second injectable microstimulator adjacent first and second contralateral thoracic nerves; and
    applying a stimulating electrical current from the injectable microstimulator to the thoracic spinal nerve at a sufficient intensity and duration to induce a forced contraction of the intercostal muscle innervated by that spinal nerve.

2. The method of claim 1, wherein the contralateral nerves are at the same thoracic level.

3. The method of claim 2, wherein the first and second injectable microstimulators are placed adjacent first and second contralateral nerves of at least three thoracic levels from T8 through T12.

4. The method of claim 3 wherein the first and second injectable microstimulators are placed adjacent first and second contralateral nerves at each of at least four thoracic levels, wherein those four thoracic levels are T9, T10, T11 and T12.

5. The method of claim 3, further comprising placing the first and second injectable microstimulators adjacent first and second contralateral L1 nerves that innervate intercostal muscles.

6. The method of claim 5, wherein the first and second injectable microstimulators are placed against first and second contralateral nerves of at least T8, T9, T10, T11, T12 and L1.

7. The method of claim 1, wherein the forced expiration is a cough.

8. The method of claim 7, wherein the subject has a spinal cord injury that impairs coughing.

9. The method of claim 1, wherein the injectable microstimulator is a single-channel microstimulator.

10. The method of claim 1, wherein the stimulating electrical current provides asymmetric biphasic constant-current pulses.

11. The method of claim 1, wherein the stimulating electrical current provides at least one of a frequency range of approximately five to approximately fifty hertz, burst lengths ranging from about a tenth of a second to about ten seconds, stimulation intensity ranging from about three to thirty milliamps, or a pulse width of about two hundred microseconds.

12. The method of claim 1, wherein the injectable microstimulator includes a first electrode and a second electrode.

13. The method of claim 1, wherein the first and second injectable microstimulators are percutaneously inserted into the subject from a surface location about two to about seven centimeters lateral to a spinous process in the subject.

14. The method of claim 1, wherein the first and second injectable microstimulators are positioned about one to about five centimeters external to the neuroforamen in the subject.

15. The method of claim 1, wherein the injectable microstimulators are independently programmable single channel stimulators allowing each microstimulator to be programmed with at least one stimulation pattern.

16. The method of claim 15, further comprising a programmable controlling device coupled to at least one of the injectable microstimulators for controlling the at least one stimulation pattern.

17. The method of claim 16, further comprising a power source coupled to the injectable microstimulators for providing energy to the injectable microstimulators, wherein the power source is a single external radio-frequency transmission coil.

18. The method of claim 1, wherein the injectable microstimulator is a wireless injectable micro stimulator.

19. The method of claim 1, further comprising identifying an implantation site for the microstimulator with an insertion tool including an electrical stimulating probe, wherein the electrical stimulating probe delivers a trial electrical current to find a microstimulator position sufficiently adjacent the spinal nerve to apply the stimulating electrical current.

20. A method of restoring cough function in a subject having a spinal cord injury that interferes with coughing, the method comprising:
percutaneously injecting a plurality of microstimulators with a microstimulator insertion system onto each of the bilateral intercostal nerves from at least T8 through L1 vertebrae in a subject, wherein the microstimulators are placed within 8 cm externally of a neuroforamen from which each spinal nerve emerges from each vertebra; and
stimulating the bilateral intercostal nerves with the plurality of microstimulators, the plurality of microstimulators providing asymmetric biphasic constant-current pulses at a sufficient intensity and duration to induce a forced contraction of intercostal muscles innervated by the stimulated spinal nerves, whereby a cough is produced.

21. The method of claim 20, wherein each of the microstimulators is a single-channel microstimulator.

22. The method of claim 20, wherein each of the plurality of microstimulators is injected from a surface location about two to about eight centimeters lateral to a spinous process of the subject, and a depth of insertion is determined by applying a test stimulus current from an electrode being injected.

23. The method of claim 20, wherein each of the plurality of microstimulators are placed within about five centimeters externally to the neuroforamen.

24. The method of claim 23, wherein the plurality of microstimulators provide an asymmetric biphasic constant-current pulse having a frequency range of approximately five to approximately fifty hertz, burst lengths ranging from about a tenth of a second to about ten seconds, stimulation intensity ranging from about three to 30 milliamps, and a pulse width of about two hundred microseconds.

* * * * *